United States Patent
Clary et al.

(10) Patent No.: US 7,807,669 B2
(45) Date of Patent: *Oct. 5, 2010

(54) BIAROMATIC COMPOUNDS WHICH ACTIVATE PPARγ TYPE RECEPTORS AND COSMETIC/PHARMACEUTICAL COMPOSITIONS COMPRISED THEREOF

(75) Inventors: Laurence Clary, La Colle sur Loup (FR); Claire Bouix-Peter, Vallauris (FR); Michel Rivier, Nice (FR); Pascal Collette, Le Connet (FR); Andre Jomard, Saint Vallier de Thiey (FR)

(73) Assignee: Galderma Research & Development, Biot (FR)

(*) Notice: Subject to any disclaimer, the term of this patent is extended or adjusted under 35 U.S.C. 154(b) by 0 days.

This patent is subject to a terminal disclaimer.

(21) Appl. No.: 12/266,096

(22) Filed: Nov. 6, 2008

(65) Prior Publication Data
US 2009/0062340 A1 Mar. 5, 2009

Related U.S. Application Data

(60) Division of application No. 11/131,302, filed on May 18, 2005, now Pat. No. 7,452,878, which is a continuation of application No. PCT/EP03/14861, filed on Nov. 18, 2003.

(60) Provisional application No. 60/454,310, filed on Mar. 14, 2003.

(30) Foreign Application Priority Data
Nov. 19, 2002 (FR) .................. 02 14465

(51) Int. Cl.
A61K 31/425 (2006.01)
A61K 31/535 (2006.01)
C07D 261/02 (2006.01)
C07D 265/28 (2006.01)
C07D 401/00 (2006.01)

(52) U.S. Cl. .................. 514/231.2; 514/364; 514/378; 544/98; 546/207; 546/208; 548/240

(58) Field of Classification Search .............. 514/231.2, 514/364, 378; 544/98; 546/207; 548/240
See application file for complete search history.

(56) References Cited

U.S. PATENT DOCUMENTS

| 6,927,228 B2 | 8/2005 | Bernardon et al. | |
| 7,157,490 B2 * | 1/2007 | Colandrea et al. | ........... 514/423 |
| 7,452,878 B2 * | 11/2008 | Clary et al. | ............... 514/231.2 |
| 7,625,914 B2 | 12/2009 | Clary et al. | |
| 2009/0012129 A1 * | 1/2009 | Boiteau et al. | ............... 514/352 |

FOREIGN PATENT DOCUMENTS

| WO | WO 0035864 A1 | 6/2000 |
| WO | WO 01/21584 A1 | 3/2001 |
| WO | WO 02/12210 A1 | 2/2002 |

OTHER PUBLICATIONS

Castanedo et al., "Solid-Phase Synthesis of Dual α4β1/α4β7 Integrin Antagonists: Two Scaffolds with Overlapping Pharmacophores", Bioorganic & Medicinal Chemistry Letters, Oct. 2002, pp. 2913-2917, vol. 12, Elsevier Science Ltd.
Sircar et al., "Synthesis and SAR of N-benzoyl-L-Biphenylalanine Derivatives: Discovery of TR-14035, A Dual α4β7/α4β1 Integrin Antagonist", Bioorganic & Medicinal Chemistry, Jun. 2002, pp. 2051-2066, vol. 10, Elsevier Science Ltd.
French Search Report corresponding to FR 02/14465, issued on Aug. 7, 2003, 3 pages.
International Search Report corresponding to PCT/EP 03/14861, issued on May 25, 2004, 5 pages.

* cited by examiner

*Primary Examiner*—Susannah Chung
(74) *Attorney, Agent, or Firm*—Buchanan Ingersoll & Rooney PC

(57) ABSTRACT

Novel biaromatic compounds having the structural formula (I) below:

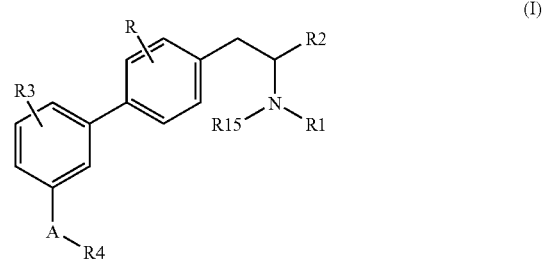

are formulated into pharmaceutical compositions suited for administration in human or veterinary medicine (in dermatology, and also in the fields of cardiovascular diseases, immune diseases and/or diseases associated with lipid metabolism), or, alternatively, into cosmetic compositions.

16 Claims, No Drawings

BIAROMATIC COMPOUNDS WHICH ACTIVATE PPARγ TYPE RECEPTORS AND COSMETIC/PHARMACEUTICAL COMPOSITIONS COMPRISED THEREOF

CROSS-REFERENCE TO PRIORITY/PCT/PROVISIONAL APPLICATIONS

This application is a divisional of U.S. application Ser. No. 11/131,302, filed May 18, 2005, which claims priority under 35 U.S.C. §119 of FR 02/14465, filed Nov. 19, 2002, and of provisional application Ser. No. 60/454,310, filed Mar. 14, 2003, and is a continuation of PCT/EP 2003/014861, filed Nov. 18, 2003 and designating the United States (published in the English language on Jun. 3, 2004 as WO 2004/046091 A3), each hereby expressly incorporated by reference and each assigned to the assignee hereof.

BACKGROUND OF THE INVENTION

1. Technical Field of the Invention

The present invention relates to a novel class of biaromatic compounds which are modulators of receptors of Peroxisome Proliferator-Activated Receptor type of subtype γ (PPAR-γ). This invention also relates to a process for the preparation thereof and to their formulation into pharmaceutical compositions suited for human or veterinary medicine, or alternatively for cosmetic compositions.

2. Description of Background and/or Related and/or Prior Art

The activity of receptors of PPAR type has been the subject of many studies. Mention may be made, as a guide, of the publication entitled "Differential Expression of Peroxisome Proliferator-Activated Receptor Subtypes During the Differentiation of Human Keratinocytes", Michel Rivier et al., *J. Invest. Dermatol.*, 111, 1998, p 1116-1121, in which are listed a large number of bibliographic references relating to receptors of PPAR type. Mention may also be made, as a guide, of the report entitled "The PPARs: From orphan receptors to Drug Discovery", Timothy M. Willson, Peter J. Brown, Daniel D. Sternbach, and Brad R. Henke, *J. Med. Chem.*, 2000, Vol. 43, p. 527-550.

PPAR receptors activate transcription by binding to elements of DNA sequences, known as peroxysome proliferator response elements (PPRE), in the form of a heterodimer with retinoid X receptors (known as RXRs).

Three subtypes of human PPARs have been identified and described: PPARα, PPARγ and PPARδ (or NUC1).

PPARα is mainly expressed in the liver, while PPARδ is ubiquitous.

PPARγ is the most extensively studied of the three subtypes. All prior art references suggest a critical role for PPARγ in regulating the differentiation of adipocytes, where it is greatly expressed. It also has a key role in systemic lipid homeostasis.

It has been described, in particular in WO 96/33724, that PPARγ-selective compounds, such as a prostaglandin-J2 or -D2, are potential active agents for treating obesity and diabetes.

Moreover, the assignee hereof has already described PPARγ compounds and/or the use thereof in the following applications. FR-2,773,075 describes the use of PPARγ-activating compounds in the preparation of a pharmaceutical composition, the composition being intended to treat skin disorders associated with an anomaly of epidermal cell differentiation. WO 01/02543 describes a novel class of PPARδ-modulating compounds.

SUMMARY OF THE INVENTION

A novel class of PPARγ-modulating compounds has now been developed that exhibit very good specific affinity for PPARγ.

Thus, the present invention features novel compounds having the general formula (I) below:

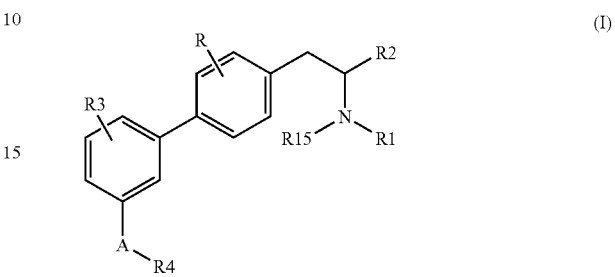

in which R is a halogen atom or a hydrogen atom; $R_1$ is a radical selected from among those of formulae a)-e):

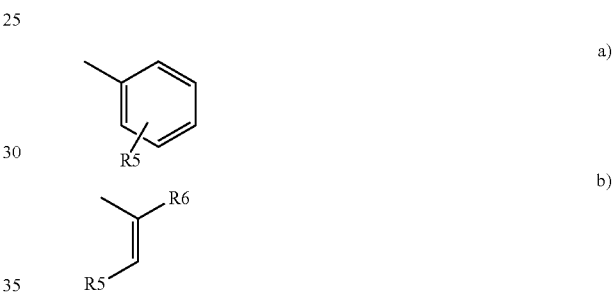

c) $-(CH_2)_m-(CO)_n-(X)_p-(CH_2)_q-R_5$, d) $-(CH_2)_m-(NR_{16})_n-(C(O,NR_{17}))_p-R_5$, e) an alpha-amino acid N-protected with standard amine-protecting groups, such as 9-fluorenylmethylcarbamate (FMOC), t-butylcarbamate (BOC), benzyl or trifluoroacetyl, wherein $R_5$, $R_6$, $R_{16}$, $R_{17}$, X, m, n, p and q are as defined below; $R_2$ is a radical selected from among those of formulae (a)-(c):

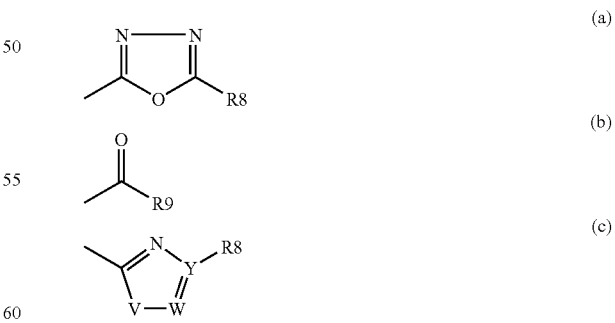

wherein $R_8$, $R_9$, V, W and Y are as defined below; $R_3$ is a hydrogen atom, a halogen atom, an alkyl radical having from 1 to 12 carbon atoms, a hydroxyl radical, an alkoxy radical having from 1 to 7 carbon atoms, a polyether radical, a nitro radical, or an amino radical that may optionally be substituted with one or more alkyl radicals having from 1 to 12 carbon atoms, an aryl radical, an aralkyl radical, a heteroaryl radical or a heterocyclic radical; $R_4$ is an alkyl radical having from 1 to 12 carbon atoms, an aryl radical, an aralkyl radical, a heteroaryl radical, a heterocyclic radical or a 9-fluorenylmethyl radical; $R_5$ is a hydrogen atom, an alkyl radical having from 1 to 12 carbon atoms, an alkoxy radical having from 1 to 7 carbon atoms, an aryl radical, an aralkyl radical, a heteroaryl radical, a heterocyclic radical or a group $(CO)_s(Z)_tR_7$, wherein Z, $R_7$, s and t are as defined below; $R_6$ is a hydrogen atom, an alkyl radical having from 1 to 12 carbon atoms; m, n, p, q, s and t have the values 0, 1 or 2; X is an oxygen or sulfur atom or $NR_7$; $R_7$ is as defined below; V is an oxygen, nitrogen or sulfur atom; W is a nitrogen atom or a radical $C-R_{11}$, wherein $R_{11}$ is as defined below; Y is a nitrogen atom or a carbon atom; Z is an oxygen, nitrogen or sulfur atom; $R_7$ is a hydrogen atom, an alkyl radical having from 1 to 12 carbon atoms, an aryl radical, an aralkyl radical, a heteroaryl radical or a heterocyclic radical; $R_8$ is a hydrogen atom, an alkyl radical having from 1 to 12 carbon atoms, an aryl radical, an aralkyl radical, a heteroaryl radical or a heterocyclic radical; $R_9$ is a radical $O-(CH_2)_v-R_{10}$, a hydroxyl radical, an alkoxy radical having from 1 to 7 carbon atoms, an aryl radical, an aralkyl radical, a heteroaryl radical, a heterocyclic radical, or the radical:

wherein $R_{10}$, R' and R" are as defined below; R' is a hydrogen atom, an alkyl radical having from 1 to 12 carbon atoms, an aryl radical, an aralkyl radical, a heteroaryl radical or a heterocyclic radical or a hydroxyl radical; R" is a hydrogen atom, an alkyl radical having from 1 to 12 carbon atoms, an aryl radical, an aralkyl radical, optionally substituted with one or more halogen atoms, a heteroaryl radical, a heterocyclic radical or a radical $(CH_2)_v-R_{10}$, wherein $R_{10}$ and v are as defined below; $R_{10}$ is an aryl, aralkyl or heteroaryl radical, a heterocyclic radical, the radical $NH-CO-R_{11}$, the radical $NH-CO-O-R_{11}$, the radical $N-R_{11}R_{12}$ or the radical $CH-R_{11}R_{12}$; v has the values 1, 2 or 3; $R_{11}$ is a hydrogen atom, an alkyl radical having from 1 to 12 carbon atoms, an aryl radical, an aralkyl radical, a heteroaryl radical or a heterocyclic radical; $R_{12}$ is a hydrogen atom or an alkyl radical having from 1 to 3 carbon atoms; A is a radical having the following structure:

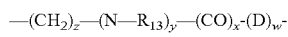

or

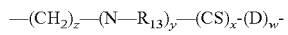

wherein D, w, x, y, z and $R_{13}$ are as defined below; D is an oxygen or sulfur atom, a radical $-NR_{14}$ or a $CH_2$ radical; $R_{14}$ is as defined below; x, y and z, which may be identical or different, have the values 0 or 1; w has a value from 0 to 6 with the proviso that w is equal to 0 or 1 when D is oxygen, and $R_{13}$ and $R_{14}$ are each a hydrogen atom or an alkyl radical having from 1 to 12 carbon atoms; $R_{15}$ is a hydrogen atom or an alkyl radical having from 1 to 7 carbon atoms; $R_{16}$ and $R_{17}$, which may be identical or different, are each a hydrogen atom, an alkyl radical having from 1 to 12 carbon atoms, an aryl radical, an aralkyl radical, a heteroaryl radical or a heterocyclic radical or a hydroxyl radical, and the optical and geometrical isomers and salts and mixtures thereof, but other than the compounds of formula (II) below:

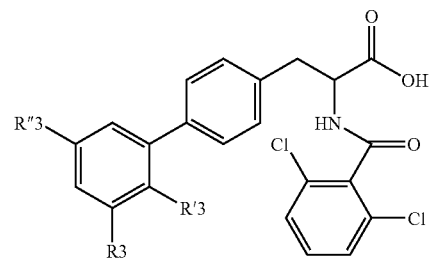

in which:

R3=OMe and R'3=R"3=H;

R3=OMe, R'3=OMe and R"3=H; and

R3=H and R'3=R"3=OMe;

also other than the compounds of formula (III) below:

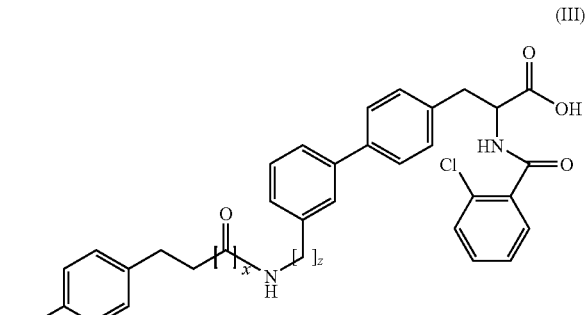

in which:

z=1 and x=0; and z=0 and x=1;

and also other than the compounds of formula (IV) below:

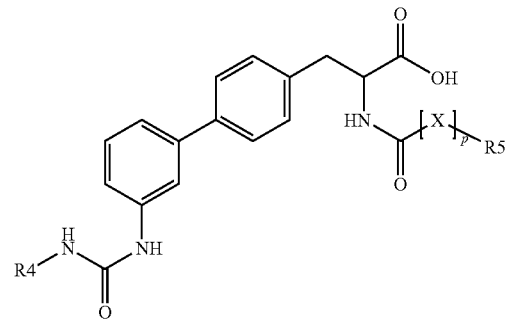

in which:

p=1, X is an oxygen atom, R5 is a benzyl radical and R4 is a 2-benzimidazole or 4-pyridine radical;

p=1, X is an oxygen atom, R5 is an ethyl radical and R4 is a 2-pyridine, 3-pyridine, 4-pyridine or methyl radical;

p=1, X is an oxygen atom, R4 is a propyl radical and R5 is an ethyl, $CH_2$-isopropyl, $CH_2$-tert-butyl, cyclopentyl, 4-methoxyphenyl or benzyl radical;

p=1, X is an NH radical, R4 is a propyl radical and R5 is a hydrogen atom or a benzyl radical;

p=1, X is an NH radical, and R4 and R5 are each a cyclohexyl radical; and p=0, R4 is an ethyl radical and R5 is a 4-methoxyphenyl radical.

DETAILED DESCRIPTION OF BEST MODE AND SPECIFIC/PREFERRED EMBODIMENTS OF THE INVENTION

In particular, when the compounds according to the invention are in the form of salts, they are salts of an alkali metal or alkaline-earth metal, zinc salts or salts of an organic amine.

According to the present invention, the term "hydroxyl radical" means an —OH radical.

According to the present invention, the expression "alkyl radical having from 1 to 3 carbon atoms", means a methyl, ethyl or propyl radical.

According to the present invention, the expression "alkyl radical having from 1 to 12 carbon atoms" means a linear or cyclic, optionally branched, radical having 1 to 12 carbon atoms, which may be interrupted with a hetero atom, and the alkyl radicals having from 1 to 12 carbon atoms are preferably methyl, ethyl, isopropyl, butyl, tert-butyl, hexyl, octyl, decyl or cyclohexyl radicals.

According to the present invention, the expression "alkyl radical having from 1 to 7 carbon atoms" means a linear or cyclic, optionally branched, radical having 1 to 7 carbon atoms, which may be interrupted with a hetero atom, and the alkyl radicals having from 1 to 7 carbon atoms are preferably methyl, ethyl, isopropyl, butyl, tert-butyl, hexyl, or heptyl radicals.

The term "polyether radical" means a polyether radical having from 1 to 6 carbon atoms interrupted with at least one oxygen atom, such as methoxymethoxy, ethoxymethoxy or methoxyethoxymethoxy radicals.

The term "halogen atom" means a fluorine, chlorine or bromine atom.

The expression "alkoxy radical having from 1 to 7 carbon atoms" means a radical having from one to seven carbon atoms, such as methoxy, ethoxy, isopropyloxy, tert-butoxy, hexyloxy, which may optionally be substituted with an alkyl radical having from 1 to 12 carbon atoms.

The term "aryl radical" means a phenyl, biphenyl, cinnamyl or naphthyl radical, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl having from 1 to 12 carbon atoms.

The term "aryloxy radical" means a phenyloxy, biphenyloxy, cinnamyloxy or naphthyloxy radical, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl having from 1 to 12 carbon atoms.

The term "aralkyl radical" means a benzyl, phenethyl or 2-naphthylmethyl radical, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl having from 1 to 12 carbon atoms.

The term "aralkoxy radical" means a benzyloxy, phenethyloxy or 2-naphthyloxy methyl radical, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl having from 1 to 12 carbon atoms.

The term "heteroaryl radical" means an aryl radical interrupted with one or more hetero atoms, such as a pyridyl, furyl, thienyl, isoxazolyl, oxadiazolyl, oxazolyl, benzimidazolyl, indolyl or benzofuran radical, optionally substituted with at least one halogen, an alkyl having from 1 to 12 carbon atoms, an alkoxy having from 1 to 7 carbon atoms, an aralkoxy radical or an aryloxy radical, an aryl radical, a nitro function, a polyether radical, an aryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl having from 1 to 12 carbon atoms.

The term "heterocyclic radical" preferably means a morpholino, piperidino, piperazino, 2-oxo-1-piperidyl or 2-oxo-1-pyrrolidinyl radical, optionally substituted with at least one alkyl having from 1 to 12 carbon atoms, an alkoxy having from 1 to 7 carbon atoms, an aralkoxy radical or an aryloxy radical, an aryl radical, a nitro function, a polyether radical, an aryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl having from 1 to 12 carbon atoms.

Among the compounds of formula (I) within the scope of the present invention, mention may in particular be made of the following compounds (alone or as a mixture):

1. ethyl (S)-2-(2-benzoylphenylamino)-3-[3'-(3-heptyl-1-methylureido)biphenyl-4-yl]propionate;
2. (S)-2-(2-benzoylphenylamino)-3-[3'-(3-heptyl-1-methylureido)biphenyl-4-yl]propionic acid;
3. (S)-1-{4'-[2-(2-benzoylphenylamino)-2-(5-propyl[1,3,4]oxadiazol-2-yl)ethyl]biphenyl-3-yl}-3-heptyl-1-methylurea;
4. ethyl (S)-2-(2-benzoylphenylamino)-3-{3'-[3-(4-dimethylaminophenyl)-1-methylureido]biphenyl-4-yl}propionate;
5. (S)-2-(2-benzoylphenylamino)-3-{3'-[3-(4-dimethylaminophenyl)-1-methylureido]biphenyl-4-yl}propionic acid;

6. (S)-2-(2-benzoylphenylamino)-3-[3'-(1-methyl-3-naphthalen-2-ylureido)biphenyl-4-yl]propionic acid;
7. isobutyl (S)-{4'-[2-(2-benzoylphenylamino)-2-(5-propyl[1,3,4]oxadiazol-2-yl)ethyl]biphenyl-3-yl}methylcarbamate;
8. (S)-2-(2-benzoylphenylamino)-3-[3'-(3-heptyl-1-methylureido)biphenyl-4-yl]-N-pentylpropionamide;
9. (S)-1-{4'-[2-(2-benzoylphenylamino)-3-(4-methylpiperid-1-yl)-3-oxopropyl]biphenyl-3-yl}-3-heptyl-1-methylurea;
10. (S)—N-(2-acetylaminoethyl)-2-(2-benzoylphenylamino)-3-[3'-(3-heptyl-1-methylureido)biphenyl-4-yl]propionamide;
11. (S)-2-(2-benzoylphenylamino)-N-benzyl-3-[3'-(3-heptyl-1-methylureido)biphenyl-4-yl]propionamide;
12. (S)-1-{2-(2-benzoylphenylamino)-3-[3'-(3-heptyl-1-methylureido)biphenyl-4-yl]propionyl}piperidine-4-carboxylic acid ethyl ester;
13. (S)-2-(2-benzoylphenylamino)-N,N-dibenzyl-3-[3'-(3-heptyl-1-methylureido)biphenyl-4-yl]propionamide;
14. (S)-1-{4'-[2-(2-benzoylphenylamino)-3-morpholin-4-yl-3-oxopropyl]biphenyl-3-yl}-3-heptyl-1-methylurea;
15. (S)-2-(2-benzoylphenylamino)-3-[3'-(3-heptyl-1-methylureido)biphenyl-4-yl]-N-(3-methylbutyl)propionamide;
16. (S)-1-{4'-[2-(2-benzoylphenylamino)-3-(4-methylpiperazin-1-yl)-3-oxopropyl]biphenyl-3-yl}-3-heptyl-1-methylurea;
17. (S)-2-(2-benzoylphenylamino)-3-[3'-(3-heptyl-1-methylureido)biphenyl-4-yl]-N-hexylpropionamide;
18. (S)-2-(2-benzoylphenylamino)-3-[3'-(3-heptyl-1-methylureido)biphenyl-4-yl]-N-pyridin-2-ylmethylpropionamide;
19. (S)-1-{4'-[2-(2-benzoylphenylamino)-3-(2,6-dimethylmorpholin-4-yl)-3-oxopropyl]biphenyl-3-yl}-3-heptyl-1-methylurea;
20. (S)-2-(2-benzoylphenylamino)-N-benzyl-3-[3'-(3-heptyl-1-methylureido)biphenyl-4-yl]-N-methylpropionamide;
21. (S)-2-(2-benzoylphenylamino)-3-[3'-(3-heptyl-1-methylureido)biphenyl-4-yl]-N-phenethylpropionamide;
22. (S)-2-(2-benzoylphenylamino)-3-[3'-(3-heptyl-1-methylureido)biphenyl-4-yl]-N-[3-(2-oxo-1-pyrrolidinyl)propyl]propionamide;
23. (S)-2-(2-benzoylphenylamino)-N-(2,5-difluorobenzyl)-3-[3'-(3-heptyl-1-methylureido)biphenyl-4-yl]propionamide;
24. tert-butyl (S)-4-{2-(2-benzoylphenylamino)-3-[3'-(3-heptyl-1-methylureido)biphenyl-4-yl]propionyl}piperazine-1-carboxylate;
25. (S)-2-(2-benzoylphenylamino)-N-butyl-3-[3'-(3-heptyl-1-methylureido)biphenyl-4-yl]propionamide;
26. (S)-2-(2-benzoylphenylamino)-N-(2-dimethylaminoethyl)-3-[3'-(3-heptyl-1-methylureido)biphenyl-4-yl]propionamide;
27. (S)-2-(2-benzoylphenylamino)-3-[3'-(3-heptyl-1-methylureido)biphenyl-4-yl]-N-methyl-N-phenethylpropionamide;
28. ethyl (S)-3-{3'-[(benzoylmethylamino)methyl]biphenyl-4-yl}-2-(2-benzoylphenylamino)propionate;
29. (S)-3-{3'-[(benzoyl methylamino)methyl]biphenyl-4-yl}-2-(2-benzoylphenylamino)propionic acid;
30. (S)—N-{4'-[2-(2-benzoylphenylamino)-2-(5-propyl[1,3,4]oxadiazol-2-yl)ethyl]biphenyl-3-ylmethyl}-N-methylbenzamide;
31. (S)-3-{3'-[(benzoyl methylamino)methyl]biphenyl-4-yl}-2-(1-methyl-3-oxo-3-phenylpropenylamino)propionic acid;
32. ethyl (S)-2-(2-{3'-[(benzoylmethylamino)methyl]biphenyl-4-yl}-1-ethoxycarbonylethylamino)benzoate;
33. (S)-2-(2-{3'-[(benzoylmethylamino)methyl]biphenyl-4-yl}-1-ethoxycarbonylethylamino)benzoic acid;
34. (S)-2-(2-{3'-[(benzoylmethylamino)methyl]biphenyl-4-yl}-1-carboxyethylamino)benzoic acid;
35. methyl (R)-3-{3'-[(benzoylmethylamino)methyl]biphenyl-4-yl}-2-(2-benzoylphenylamino)propionate;
36. (R)-3-{3'-[(benzoyl methylamino)methyl]biphenyl-4-yl}-2-(2-benzoylphenylamino)propionic acid;
37. 3-{3'-[(benzoylmethylamino)methyl]biphenyl-4-yl}-2-tert-butoxycarbonylaminopropionic acid;
38. 3-{3'-[(benzoylmethylamino)methyl]biphenyl-4-yl}-2-(1-methyl-3-oxo-3-phenylpropenylamino)propionic acid;
39. butyl (S)-2-(2-benzoylphenylamino)-3-[3'-(3-heptyl-1-methylureido)biphenyl-4-yl]propionate;
40. hexyl (S)-2-(2-benzoylphenylamino)-3-[3'-(3-heptyl-1-methylureido)biphenyl-4-yl]propionate;
41. benzyl (S)-2-(2-benzoylphenylamino)-3-[3'-(3-heptyl-1-methylureido)biphenyl-4-yl]propionate;
42. phenethyl (S)-2-(2-benzoylphenylamino)-3-[3'-(3-heptyl-1-methylureido)biphenyl-4-yl]propionate;
43. 2-ethylhexyl (S)-2-(2-benzoylphenylamino)-3-[3'-(3-heptyl-1-methylureido)biphenyl-4-yl]propionate;
44. 2-morpholin-4-ylethyl (S)-2-(2-benzoylphenylamino)-3-[3'-(3-heptyl-1-methylureido)biphenyl-4-yl]propionate;
45. 3-methoxybenzyl (S)-2-(2-benzoylphenylamino)-3-[3'-(3-heptyl-1-methylureido)biphenyl-4-yl]propionate;
46. 2-naphthylmethyl (S)-2-(2-benzoylphenylamino)-3-[3'-(3-heptyl-1-methylureido)biphenyl-4-yl]propionate;
47. 2-(5-methyl-2-phenyloxazol-4-yl)ethyl (S)-2-(2-benzoylphenylamino)-3-[3'-(3-heptyl-1-methylureido)biphenyl-4-yl]propionate;
48. (S,S)-2-(2-amino-4-methylsulfanylbutyrylamino)-3-[3'-(methylnonanoylamino)biphenyl-4-yl]propionic acid;
49. (S)-2-butyrylamino-3-[3'-(methylnonanoylamino)biphenyl-4-yl]propionic acid;
50. (S)-3-[3'-(methylnonanoylamino)biphenyl-4-yl]-2-(3-phenylpropionylamino)propionic acid;
51. (S)-3-[3'-(methylnonanoylamino)biphenyl-4-yl]-2-(4-oxopentanoylamino)propionic acid;
52. (S)-2-(3-methoxybenzoylamino)-3-[3'-(methylnonanoylamino)biphenyl-4-yl]propionic acid;
53. (S)-2-(4-methoxybenzoylamino)-3-[3'-(methylnonanoylamino)biphenyl-4-yl]propionic acid;
54. methyl (S)—N-{1-carboxy-2-[3'-(methylnonanoylamino)biphenyl-4-yl]ethyl}isophthalamate;
55. (S)-2-(3-benzoylbenzoylamino)-3-[3'-(methylnonanoylamino)biphenyl-4-yl]propionic acid;
56. (S)-3-[3'-methylnonanoylamino)biphenyl-4-yl]-2-(2-piperid-4-ylacetylamino)propionic acid;
57. (S,S)-2-(2-amino-3-phenylpropionylamino)-3-[3'-(methylnonanoylamino)biphenyl-4-yl]propionic acid;
58. (S)-2-(2-methoxybenzoylamino)-3-[3'-(methylnonanoylamino)biphenyl-4-yl]propionic acid;
59. (S)-2-benzylamino-3-[3'-(3-heptyl-1-methylureido)biphenyl-4-yl]propionic acid;
60. (S)-3-[3'-(3-heptyl-1-methylureido)biphenyl-4-yl]-2-(2-methoxybenzylamino)propionic acid;
61. methyl (S)-4-({1-carboxy-2-[3'-(3-heptyl-1-methylureido)biphenyl-4-yl]ethylamino}methylbenzoate;
62. (S)-2-(4-dimethylaminobenzylamino)-3-[3'-(3-heptyl-1-methylureido)biphenyl-4-yl]propionic acid;
63. (S)-2-(3,4-dimethoxybenzylamino)-3-[3'-(3-heptyl-1-methylureido)biphenyl-4-yl]propionic acid;
64. (S)-2-(4-butoxybenzylamino)-3-[3'-(3-heptyl-1-methylureido)biphenyl-4-yl]propionic acid;

65. (S)-3-[3'-(3-heptyl-1-methylureido)biphenyl-4-yl]-2-(3-phenylallylamino)propionic acid;
66. (S)-3-[3'-(3-heptyl-1-methylureido)biphenyl-4-yl]-2-[(1-naphthylmethyl)amino]propionic acid;
67. (S)-2-(4-tert-butylbenzylamino)-3-[3'-(3-heptyl-1-methylureido)biphenyl-4-yl]propionic acid;
68. (S)-3-[3'-(3-heptyl-1-methylureido)biphenyl-4-yl]-2-[(2-naphthylmethyl)amino]propionic acid;
69. (S)-3-[3'-(3-heptyl-1-methylureido)biphenyl-4-yl]-2-(3-phenoxybenzylamino)propionic acid;
70. (S)-3-[3'-(3-heptyl-1-methylureido)biphenyl-4-yl]-2-[(pyridin-4-ylmethyl)amino]propionic acid;
71. (S)-3-[3'-(3-heptyl-1-methylureido)biphenyl-4-yl]-2-pentylaminopropionic acid;
72. (S)-3-[3'-(3-heptyl-1-methylureido)biphenyl-4-yl]-2-phenethylaminopropionic acid;
73. (S)-3-[3'-(3-heptyl-1-methylureido)biphenyl-4-yl]-2-[(1-methyl-1H-pyrrol-2-ylmethyl)amino]propionic acid;
74. (S)-2-(2-ethylbutylamino)-3-[3'-(3-heptyl-1-methylureido)biphenyl-4-yl]propionic acid;
75. (S)-2-(cyclohexylmethylamino)-3-[3'-(3-heptyl-1-methylureido)biphenyl-4-yl]propionic acid;
76. (S)-3-[3'-(3-heptyl-1-methylureido)biphenyl-4-yl]-2-[(3-methylthiophen-2-ylmethyl)amino]propionic acid;
77. (S)-2-[(benzofuran-2-ylmethyl)amino]-3-[3'-(3-heptyl-1-methylureido)biphenyl-4-yl]propionic acid;
78. (S)-2-(2-benzoylphenylamino)-3-{3'-[(4-dimethylaminobenzoyl)methylamino]biphenyl-4-yl}propionic acid;
79. (S)-2-(2-benzoylphenylamino)-3-{3'-[methyl(naphthalene-2-carbonyl)amino]biphenyl-4-yl}propionic acid;
80. (S)-2-(2-benzoylphenylamino)-3-[3'-(methyloctanoylamino)biphenyl-4-yl]propionic acid;
81. ethyl 4-(3-{1-carboxy-2-[3'-(3-heptyl-1-methylureido)biphenyl-4-yl]ethyl}ureido)benzoate;
82. (S)-3-[3'-(3-heptyl-1-methylureido)biphenyl-4-yl]-2-(3-phenylureido)propionic acid;
83. (S)-2-butyrylamino-3-{3'-[methyl-(2-naphthalen-2-ylacetyl)amino]biphenyl-4-yl}propionic acid;
84. (S)-2-butyrylamino-3-{3'-[methyl(naphthalene-2-carbonyl)amino]biphenyl-4-yl}propionic acid;
85. (S)-2-butyrylamino-3-[3'-(hexanoylmethylamino)biphenyl-4-yl]propionic acid;
86. (S)-2-(2-benzoylphenylamino)-3-[3'-(3-benzyl-1-methylureido)biphenyl-4-yl]propionic acid;
87. ethyl (S)-4-(3-{4'-[2-(2-benzoylphenylamino)-2-carboxyethyl]biphenyl-3-yl}-3-methylureido)benzoate;
88. (S)-2-(2-benzoylphenylamino)-3-[3'-(1-methyl-3-phenethylureido)biphenyl-4-yl]propionic acid;
89. (S)-2-(2-benzoylphenylamino)-3-[3'-(1-methyl-3-naphthalen-2-ylureido)biphenyl-4-yl]propionic acid;
90. (S)-2-(2-benzoylphenylamino)-3-{3'-[3-(4-butoxyphenyl)-1-methylureido]biphenyl-4-yl}propionic acid;
91. (S)-2-(2-benzoylphenylamino)-3-{3'-[3-(4-dimethylaminophenyl)-1-methylureido]biphenyl-4-yl}propionic acid;
92. (S)-2-(2-benzoylphenylamino)-3-[3'-(1-methyl-3-naphthalen-1-ylureido)biphenyl-4-yl]propionic acid;
93. (S)-2-(2-benzoylphenylamino)-3-[3'-(3-biphenyl-4-yl-1-methylureido)biphenyl-4-yl]propionic acid;
94. (S)-2-(2-benzoylphenylamino)-3-{3'-[1-methyl-3-(4-phenoxyphenyl)ureido]biphenyl-4-yl}propionic acid;
95. (S)-2-(2-benzoylphenylamino)-3-{3'-[3-(4-heptyloxyphenyl)-1-methylureido]biphenyl-4-yl}propionic acid;
96. (S)-2-benzoylamino-3-[3'-(3-heptyl-1-methylureido)biphenyl-4-yl]propionic acid;
97. (S)-3-{3'-[3-(4-butylphenyl)-1-methylureido]biphenyl-4-yl}-2-butyrylaminopropionic acid;
98. (S)-3-{3'-[3-(4-butylphenyl)-1-methylureido]biphenyl-4-yl}-2-(3-phenylpropionylamino)propionic acid;
99. (S)-2-benzoylamino-3-{3'-[3-(4-butylphenyl)-1-methylureido]biphenyl-4-yl}propionic acid;
100. (S)-2-(2-benzoylphenylamino)-3-{3'-[(methyloctanoylamino)methyl]biphenyl-4-yl}propionic acid;
101. (R)-2-(2-benzoylphenylamino)-3-{3'-[(methyloctanoylamino)methyl]biphenyl-4-yl}propionic acid;
102. (S)-2-(2-benzoylphenylamino)-3-{4'-fluoro-3'-[(methyloctanoylamino)methyl]biphenyl-4-yl}propionic acid;
103. (S)-2-(2-benzoylphenylamino)-3-{2'-fluoro-5'-[(methyloctanoylamino)methyl]biphenyl-4-yl}propionic acid;
104. (S)-2-(2-benzoylphenylamino)-3-(3'-{[(3-hydrazinocarbonylpropionyl)methylamino]methyl}biphenyl-4-yl}propionic acid;
105. 2-(2-benzoylphenylamino)-3-(3'-{[methyl-(5-oxohexanoyl)amino]methyl}biphenyl-4-yl)propionic acid;
106. (S)-2-[(2-benzoylphenyl)methylamino]-3-[3'-(3-heptyl-1-methylureido)biphenyl-4-yl]propionic acid;
107. (S)-2-[(2-benzoylphenyl)methylamino]-3-[3'-(1-methyl-3-naphthalene-2-ylureido)biphenyl-4-yl]propionic acid;
108. (S)-2-ethylamino-3-[3'-(3-heptyl-1-methylureido)biphenyl-4-yl]propionic acid;
109. 2-ethylamino-3-[3'-(1-methyl-3-naphthalen-2-ylureido)biphenyl-4-yl]propionic acid;
110. 3-[3'-(1-methyl-3-naphthalen-2-ylureido)biphenyl-4-yl]-2-phenylaminopropionic acid;
111. methyl (S)-2-{1-carboxy-2-[3'-(1-methyl-3-naphthalen-2-ylureido)biphenyl-4-yl]ethylamino}benzoate;
112. (S)-2-{1-carboxy-2-[3'-(1-methyl-3-naphthalen-2-ylureido)biphenyl-4-yl]ethylamino}benzoic acid;
113. 2-{1-carboxy-2-[3'-(3-heptyl-1-methylureido)biphenyl-4-yl]ethylamino}benzoic acid;
114. methyl 2-{1-carboxy-2-[3'-(3-heptyl-1-methylureido)biphenyl-4-yl]ethylamino}benzoate;
115. 3-[3'-(3-heptyl-1-methylureido)biphenyl-4-yl]-2-(2-methoxyphenylamino)propionic acid;
116. (S)-2-(2-methoxyphenylamino)-3-[3'-(1-methyl-3-naphthalen-2-ylureido)biphenyl-4-yl]propionic acid;
117. (S)-1-{4'-[2-ethylamino-3-(4-methylpiperid-1-yl)-3-oxopropyl]biphenyl-3-yl}-1-methyl-3-naphthalen-2-ylurea;
118. (S)-1-{4'-[2-ethylamino-3-(4-methylpiperid-1-yl)-3-oxopropyl]biphenyl-3-yl}-3-heptyl-1-methylurea;
119. 2-(ethylmethylamino-3-[3'-(3-hexyl-1-methylureido)biphenyl-4-yl]propionic acid;
120. 2-(S)-(2-benzoyl phenylamino)-3-[3'-(1-methyl-3-pentylureido)biphenyl-4-yl]propionic acid;
121. 2-(S)-(2-benzoylphenylamino)-3-[3'-(1-methyl-3-pentylthioureido)biphenyl-4-yl]propionic acid;
122. 2-(S)-(2-benzoylphenylamino)-3-[3'-(3-hexyl-1-methylthioureido)biphenyl-4-yl]propionic acid;
123. 2-(S)-(2-benzoylphenylamino)-3-[3'-(3-heptyl-1-methylureido)biphenyl-4-yl]-N-hydroxypropionamide;
124. 2-(2-benzoylphenylamino)-3-[3-fluoro-3'-(3-heptyl-1-methylureido)biphenyl-4-yl]propionic acid;
125. (S)-3-[3'-(3-heptyl-1-methylureido)biphenyl-4-yl]-2-propylaminopropionic acid;
126. 2-(S)-(cyclopropylmethylamino)-3-[3'-(3-heptyl-1-methylureido)biphenyl-4-yl]propionic acid;
127. 2-(S)-(cyclopropylmethylamino)-3-[3'-(1-methyl-3-pentylureido)biphenyl-4-yl]propionic acid;
128. 2-(S)-(cyclopropylmethylamino)-3-[3'-(1-methyl-3-pentylureido)biphenyl-4-yl]propionic acid;
129. 2-(S)-(cyclopropylmethylamino)-3-[3'-(1-methyl-3-naphthalen-2-ylureido)biphenyl-4-yl]propionic acid;

130. 2-(S)-(cyclopropylmethylamino)-3-[3'-(1-methyl-3-naphthalen-2-ylureido)biphenyl-4-yl]propionic acid;
131. 2-(S)-benzylamino-3-[3'-(1-methyl-3-pentylureido)biphenyl-4-yl]propionic acid;
132. 1-[4'-(2-ethylamino-3-morpholin-4-yl-3-oxopropyl)biphenyl-3-yl]-1-methyl-3-pentylurea;
133. 1-{4'-[2-ethylamino-3-(4-methylpiperazin-1-yl)-3-oxopropyl]biphenyl-3-yl}-1-methyl-3-pentylurea.

According to the present invention, the compounds of formula (I) that are more particularly preferred are those having at least one of the following characteristics:

R and $R_3$, independently of each other represent a hydrogen atom or a fluorine atom;

$R_{15}$ is an hydrogen atom or a methyl radical;

$R_1$ is the radical of formula (a) where $R_5$ is preferably a benzoyl radical, an alkyl ester radical or the group $(CO)_s(Z)_tR_7$ wherein s=1 and t=0, $R_7$ is an aryl radical or $R_1$ is the radical of formula (c) wherein m and p=0 or n and p=0;

$R_2$ is the radical of formula (a) where $R_8$ is preferably an alkyl radical or the radical of formula (b) wherein $R_9$ is preferably a hydroxyl radical or a radical NR'R";

A is the linking radical of structure —$CH_2$—$N(R_{13})$—CO— or $N(R_{13})$—$(CO)_x(D)_w$, wherein w=0 or 1 and x=0 or 1; and $R_4$ is an alkyl or aryl radical.

According to the present invention, the compounds of formula (I) that are more specifically preferred are those having at least one of the following characteristics:

R and $R_3$, independently of each other represent an hydrogen atom or a fluorine atom;

$R_{15}$ is an hydrogen atom or a methyl radical;

$R_1$ is the radical of formula (a) wherein $R_5$ is the group $(CO)_s(Z)_tR_7$ wherein s=1 and t=0, $R_7$ is an aryl radical;

$R_2$ is the radical of formula (b) wherein $R_9$ is a hydroxyl radical;

A is the linking radical of structure —$CH_2$—$N(R_{13})$—CO— or $N(R_{13})_y$—$(CO)_x(D)_w$, wherein y=1, w=1 and x=1, D is a radical —$NR_{14}$ and $R_{14}$ is a hydrogen atom;

$R_4$ is a naphthyl radical.

A general description of the preparation of the compounds of general formulae 9 to 13 of the FIGURE of Drawing is given below.

Intermediate 3 is prepared, for example, using the brominated function of compound 2 (X=Br) or a trifluoromethanesulfonyl function of 2 (X=OTf) by a Suzuki coupling with boronic acid derivatives 1, catalysed for example by tetrakistriphenylphosphinopalladium.

When R'''=CHO, compound 5 can be prepared by reductive amination with an amine $H_2NR_{14}$.

Intermediates 4 and 8 can be prepared after deprotection of the amine (—HNG') by condensation with a ketone so as to form an enamine, followed, if the ketone is a cyclohexanone, by an aromatization in the presence for example of palladium on charcoal, or else by amidation on an acid or acid halide, by addition to an isocyanate, or reductive amination on an aldehyde.

Compounds 6 and 7, if D=N, are for example synthesized by addition to an isocyanate O=C=N—$R_3$ and, if D=C, by condensation with an acid or an acid halide.

Compound 9 can be prepared, depending on the nature of R, by saponification or debenzylation.

The heterocyclic compounds 10 and 11 are synthesized by standard methods for synthesizing heterocycles, with, for example, in the case of compounds 11, condensation of hydrazine followed by the addition of an orthoester in acidic medium.

The esters 12 can be prepared, for example, by esterification with $HO(CH_2)_vR_{11}$ alcohols.

The compounds 13 are obtained by amidation reaction with an amine of HNR'R" type.

The compounds according to the invention exhibit modulatory properties of receptors of PPAR type. This activity on the PPARα, δ and γ receptors is measured in a transactivation assay and quantified via the dissociation constant Kdapp (apparent), as described in Example 48.

The preferred compounds of the present invention have a dissociation constant of less than or equal to 500 nM, and advantageously less than or equal to 100 nM.

Preferably, the compounds are modulators of receptors of specific PPARγ type, i.e., they have a ratio of the Kdapp for the PPARα and PPARδ receptors to the Kdapp for the PPARγ receptors of greater than or equal to 10. Preferably, this PPARγ/PPARα or PPARγ/PPARδ ratio is greater than or equal to 50, and more advantageously greater than or equal to 100.

The present invention also features medicinal products comprising the compounds of formula (I) as described above The present invention also features administration of the compounds of formula (I) to regulate and/or restore the metabolism of skin lipids.

The compounds according to the invention are particularly suitable in the following fields of treatment:

1) for treating dermatological afflictions or conditions associated with a keratinization disorder relating to differentiation and to proliferation, in particular for treating common acne, comedo-type acne, polymorphic acne, rosacea, nodulocystic acne, acne conglobata, senile acne and secondary acne such as solar, drug-related or occupational acne, 2) for treating other types of keratinization disorder, in particular ichthyoses, ichthyosiform conditions, Darrier's disease, palmoplantar keratoderma, leukoplakia and leukoplakiform conditions, and cutaneous or mucosal (oral) lichen, 3) for treating other dermatological afflictions or conditions having an inflammatory immunoallergic component, with or without a cell proliferation disorder, and in particular all the forms of psoriasis, whether cutaneous, mucosal or ungual psoriasis, and even psoriatic rheumatism, or alternatively cutaneous atopy, such as eczema, or respiratory atopy or else gingival hypertrophy, 4) for treating all dermal or epidermal proliferations, whether benign or malignant, whether or not of viral origin, such as common warts, flat warts and epidermodysplasia verruciformis, oral or florid papillomatoses, T lymphoma, and proliferations which may be induced by ultraviolet light, in particular in the case of basal cell and spinocellular epithelioma, and also any precancerous skin lesion such as keratoacanthomas, 5) for treating other dermatological disorders such as immune dermatoses, such as lupus erythematosus, bullous immune diseases and collagen diseases, such as scleroderma, 6) in the treatment of dermatological or systemic afflictions or conditions having an immunological component, 7) in the treatment of skin disorders due to exposure to UV radiation, and also for repairing or combating aging of the skin, whether light-induced or chronological aging, or for reducing actinic keratoses and pigmentations, or any pathological conditions associated with chronological or actinic aging, such as xerosis, 8) for combating sebaceous function disorders such as the hyperseborrhoea of acne or simple seborrhoea or seborrheoic dermatitis, 9) for preventing or treating cicatrization disorders or for preventing or repairing stretch marks, 10) in the treatment of pigmentation disorders, such as hyperpigmentation, melasma, hypopigmentation or vitiligo, 11) in the treatment of lipid metabolism afflictions or conditions, such as obesity, hyperlipidaemia, non-insulin-dependent diabetes or syndrome X, 12) in the treatment of inflammatory afflictions or conditions such as arthritis, 13) in the treatment or prevention of cancerous or precancerous conditions, 14) in the prevention or treatment of alopecia of various origins, in particular alopecia caused by chemotherapy or radiation, 15) in the treatment of disorders of the immune system, such as asthma, type I sugar diabetes, multiple sclerosis or other selective dysfunctions of the immune system, or 16) in the treatment of afflictions or conditions of the cardiovascular system, such as arteriosclerosis or hypertension.

The present invention also features pharmaceutical or cosmetic compositions comprising, in a physiologically acceptable medium, at least one compound of formula (I) as defined above.

The compositions according to the invention may be administered enterally, parenterally, topically or ocularly. The pharmaceutical composition is preferably packaged in a form which is suitable for topical application.

Via the enteral route, the composition, more particularly the pharmaceutical composition, may be in the form of tablets, filled capsules, sugar-coated tablets, syrups, suspensions, solutions, powders, granules, emulsions, or lipid or polymer vesicles or nanospheres or microspheres allowing controlled release. Via the parenteral route, the composition may be in the form of solutions or suspensions for infusion or for injection.

The compounds according to the invention are generally administered at a daily dose of approximately 0.001 mg/kg to 100 mg/kg of body weight, in 1 to 3 dosage intakes.

The compounds are used systemically at a concentration generally of from 0.001 to 10% by weight, preferably from 0.01 to 1% by weight, relative to the weight of the composition.

Via the topical route, the pharmaceutical composition according to the invention is more particularly intended for treating the skin and mucous membranes and may be in the form of ointments, creams, milks, salves, powders, impregnated pads, syndets, solutions, gels, sprays, foams, suspensions, lotions, sticks, shampoos or washing bases. It may also be in the form of lipid or polymer vesicles or nanospheres or microspheres or polymer patches and hydrogels allowing controlled release. This topical-route composition may be in anhydrous form, in aqueous form or in the form of an emulsion.

The compounds are used topically at a concentration generally from 0.001 to 10% by weight, preferably from 0.01 to 1% by weight, relative to the total weight of the composition.

The compounds of formula (I) according to the invention also find an application in the cosmetic field, in particular in body and hair hygiene and more particularly for regulating and/or restoring the metabolism of skin lipids.

This invention therefore also features the cosmetic use of a composition comprising, in a physiologically acceptable support, at least one of the compounds of formula (I), for body or hair hygiene.

The cosmetic composition according to the invention containing, in a cosmetically acceptable support, at least one compound of formula (I) or an optical or geometrical isomer or salt thereof, may in particular be in the form of a cream, a milk, a lotion, a gel, suspensions of lipid or polymer vesicles or nanospheres or microspheres, impregnated pads, solutions, sprays, mousses, sticks, soaps, shampoos or washing bases.

The concentration of the compound of formula (I) in the cosmetic composition is from 0.001 to 3% by weight relative to the total weight of the composition.

The pharmaceutical and cosmetic compositions as described above may also contain inert additives or even pharmacodynamically active additives as regards the pharmaceutical compositions, or combinations of these additives, and in particular:

wetting agents;
flavor enhancers;
preservatives such as para-hydroxybenzoic acid esters;
stabilizers;
humidity regulators;
pH regulators;
osmotic pressure modifiers;
emulsifiers;
UV-A and UV-B screening agents;
antioxidants, such as α-tocopherol, butylhydroxyanisole or butylhydroxytoluene, super oxide dismutase, ubiquinol or certain metal-chelating agents;
depigmenting agents such as hydroquinone, azeleic acid, caffeic acid or kojic acid;
emollients;
moisturizers, for instance glycerol, PEG 400, thiamorpholinone and derivatives thereof, or urea;
antiseborrheic or antiacne agents, such as S-carboxymethylcysteine, S-benzylcysteamine, salts thereof or derivatives thereof, or benzoyl peroxide;
antibiotics, for instance erythromycin and its esters, neomycin, clindamycin and its esters, and tetracyclins;
antifungal agents such as ketoconazole or polymethylene-4,5-isothiazolidones-3;
agents for promoting hair regrowth, for instance Minoxidil (2,4-diamino-6-piperidinopyrimidine-3-oxide) and its derivatives, diazoxide (7-chloro-3-methyl-1,2,4-benzothiadiazine 1,1-dioxide) and phenyloin (5,4-diphenylimidazolidine-2,4-dione);
non-steroidal anti-inflammatory agents;
carotenoids, and in particular β-carotene;
antipsoriatic agents such as anthraline and its derivatives;
eicosa-5,8,11,14-tetraynoic acid and eicosa-5,8,11-triynoic acid, and esters and amides thereof;
retinoids, i.e., natural or synthetic RAR or RXR receptor ligands;
corticosteroids or oestrogens;
α-hydroxy acids and α-keto acids or derivatives thereof, such as lactic acid, malic acid, citric acid, glycolic acid, mandelic acid, tartaric acid, glyceric acid or ascorbic acid, and also the salts, amides or esters thereof, or β-hydroxy acids or derivatives thereof, such as salicylic acid and also the salts, amides or esters thereof;
ion-channel blockers such as potassium-channel blockers;
or else, more particularly for the pharmaceutical compositions, in combination with medicinal products known to interfere with the immune system (for example cyclosporin, FK 506, glucocorticoids, monoclonal antibodies, cytokines or growth factors, etc.).

Of course, one skilled in this art will take care to choose the optional compound(s) to be added to these compositions such that the advantageous properties intrinsically associated with the present invention are not, or are not substantially, adversely affected by the envisaged addition.

Several examples of the production of active compounds of formula (I) according to the invention, and also biological activity results for such compounds and various specific formulations based on its compounds, will now be given, it being understood that same are intended only as illustrative and in nowise limitative. In said examples to follow, all parts and percentages are given by weight, unless otherwise indicated.

EXAMPLE 1

Synthesis of ethyl (S)-2-(2-benzoylphenylamino)-3-[3'-(3-heptyl-1-methylureido)biphenyl-4-yl]propionate a. Preparation of ethyl (S)-2-tert-butoxycarbonylamino-3-(4-hydroxyphenyl)propionate The preparation of this compound is described in the literature (Houlihan, F.; Bouchard, F.; Frechet, J. M. J.; Wilson, C. G.; *Can. J. Chem.*, 1985, 63, 153) from ethyl (S)-2-amino-3-(4-hydroxyphenyl)propionate, a commercial product.

b. Preparation of ethyl (S)-2-tert-butoxycarbonylamino-3-(4-trifluoromethanesulfonyloxyphenyl)propionate 1 g (8.1 mmol) of 4-dimethylaminopyridine and 62 ml (447 mmol) of triethylamine are added to a solution containing 126 g (406 mmol) of ethyl (S)-2-tert-butoxycarbonylamino-3-(4-hydroxyphenyl)propionate in 1.3 l of DCM. The reaction medium is cooled to −72° C. and 76 ml (449 mmol) of triflic anhydride are added dropwise (t=45 min). After a return to ambient temperature, 250 ml of a saturated ammonium chloride solution are added. After separation by settling out, the organic phase is recovered and the solvents are evaporated off. The residue obtained, dissolved in DCM, is filtered over 600 ml of silica. 162 g of expected triflate are obtained with a 90% yield.

c. Preparation of tert-butyl (3-bromophenyl)methylcarbamate

The preparation of this compound is described in a Glaxo Wellcome patent (Sherril, R., WO 99/65870, (23 Dec. 1999)), from 3-bromoaniline, a commercial product.

d. Preparation of tert-butyl (3-boronic acid-phenyl)methylcarbamate 315 ml (787 mmol) of 2.5 M nBuLi in hexane are added dropwise (t=1 h 30) to a solution containing 150 g (524 mmol) of tert-butyl (3-bromo-phenyl)methylcarbamate in 1.5 l of THF cooled to −78° C. 88 ml (785 mmol) of trimethyl borate are then added slowly (t=30 min) at −78° C., followed by the addition (t=10 min) of 1.2 l of an aqueous 1N hydrochloric acid solution. After a return to ambient temperature, the organic phase is recovered and the aqueous phase is extracted with 1.2 l of ethyl acetate. All the organic phases are pooled and the solvents are evaporated off. The crude product is used without purification in the following step.

e. Preparation of ethyl (S)-2-tert-butoxycarbonylamino-3-[3'-(tert-butoxycarbonylmethylamino)biphenyl-4-yl]propionate 142 g (321 mmol) of ethyl (S)-2-tert-butoxycarbonylamino-3-(4-trifluoromethanesulfonyloxyphenyl)propionate, 132 g (524 mmol) of tert-butyl (3-boronic acid-phenyl)methylcarbamate, 14.9 g (352 mmol) of lithium chloride, 400 ml (800 mmol) of a 2M potassium carbonate solution and 37.2 g (32 mmol) of tetrakis palladium are introduced into 1.4 l of toluene under a nitrogen atmosphere. The reaction medium is heated at 84° C. for 35 min and then cooled and filtered through celite. After separation by settling out, the organic phase is washed with 800 ml of water and the solvents are evaporated off. The residue obtained, dissolved in dichloromethane, is filtered through silica. After concentration, the crude product is purified by chromatography on 1.4 kg of silica with a 9/1 heptane/ethyl acetate mixture. 160 g of coupled product is obtained with a 30% yield.

f. Preparation of ethyl (S)-2-amino-3-(3'-methylaminobiphenyl-4-yl)propionate 15 g (30.0 mmol) of (S)-2-tert-butoxycarbonylamino-3-[3'-(tert-butoxycarbonylmethylamino)biphenyl-4-yl]propionate are dissolved in 150 ml of dichloromethane. 35 ml (450 mmol) of trifluoroacetic acid are added in small amounts. The medium is stirred for 12 h and then brought to pH 9 with sodium carbonate, extracted with dichloromethane, dried over magnesium sulfate, and concentrated. The residue obtained is purified by chromatography on a column of silica and eluted with a 1/1 heptane/ethyl acetate mixture. 7.7 g of expected diamine are obtained with an 87% yield.

g. Preparation of ethyl (S)-2-(2-benzoylphenylamino)-3-(3'-methylaminobiphenyl-4-yl)propionate 5.7 g (22.1 mmol) of ethyl (S)-2-amino-3-(3'-methylaminobiphenyl-4-yl)propionate and 5.8 g (28.7 mmol) of 2-benzoylcyclohexanone are dissolved in 10 ml of anisole. 0.6 g of 10% palladium-on-charcoal are added and the reaction medium is then refluxed using a Dean-Stark apparatus for 16 h. The cooled reaction medium is filtered through celite, rinsed with ethyl acetate and concentrated. The residue obtained is purified by chromatography on a column of silica and eluted with a 7/3 heptane/ethyl acetate mixture. 5.9 g of desired product are isolated with a 49% yield.

h. Synthesis of ethyl (S)-2-(2-benzoylphenylamino)-3-[3'-(3-heptyl-1-methylureido)biphenyl-4-yl]propionate 1 g (2.1 mmol of ethyl (S)-2-(2-benzoylphenylamino)-3-(3'-methylaminobiphenyl-4-yl)propionate is dissolved in 10 ml of dichloromethane. 0.58 ml (4.2 mmol) of triethylamine and 0.6 ml (3.8 mmol) of heptylisocyanate are added. The medium is stirred for 12 h and then hydrolysed, extracted with dichloromethane, dried over magnesium sulfate, and concentrated. The residue obtained is purified by chromatography on a column of silica and eluted with a 7/3 heptane/ethyl acetate mixture. 1 g of ethyl (S)-2-(2-benzoylphenylamino)-3-[3'-(3-heptyl-1-methylureido)biphenyl-4-yl]propionate is obtained with a 79% yield.

$^1$H NMR (CDCl$_3$) 0.86 (t, J=8 Hz, 3H); 1.32-1.22 (unresolved peak, 11H); 1.42 (unresolved peak, J=8 Hz, 2H); 3.33-3.15 (unresolved peak, 7H); 4.12 (unresolved peak, J=4 Hz, 2H); 4.47 (unresolved peak, 1H); 6.61 (t, J=8 Hz, 1H); 6.70 (d, J=8 Hz, 1H); 7.62-7.39 (unresolved peak, 14H); 8.96 (d, J=8 Hz, 1H)

EXAMPLE 2

Synthesis of (S)-2-(2-benzoylphenylamino)-3-[3'-(3-heptyl-1-methylureido)biphenyl-4-yl]propionic acid 0.75 g (1.2 mmol) of ethyl (S)-2-(2-benzoylphenylamino)-3-[3'-(3-heptyl-1-methylureido)biphenyl-4-yl]propionate (Example 1H) is dissolved in a mixture of 10 ml of tetrahydrofuran, 1 ml of methanol and a few drops of water. 86 mg (2 mmol) of lithium hydroxide are added. The medium is stirred for 6 h and then treated with an aqueous 1N hydrochloric acid solution, extracted with ethyl acetate, dried over magnesium sulfate, and concentrated. The residue obtained is purified by chromatography on a column of silica and eluted with a 1/1 heptane/ethyl acetate mixture. 0.55 g of (S)-2-(2-benzoylphenylamino)-3-[3'-(3-heptyl-1-methylureido)biphenyl-4-yl)propionic acid is obtained with a 77% yield.

$^1$H NMR (CDCl$_3$) 0.85 (t, J=8 Hz, 3H); 1.28-1.22 (unresolved peak, 8H); 1.39 (unresolved peak, J=8 Hz, 2H); 3.16 (unresolved peak, J=8 Hz, 2H); 3.28 (s, 3H); 3.42 (unresolved peak, J=4 Hz, 2H); 4.41 (t, J=4 Hz, 1H); 6.61 (t, J=8 Hz, 1H); 6.71 (d, J=8 Hz, 1H); 7.62-7.20 (unresolved peak, 14H); 8.96 (unresolved peak, 1H)

Melting point: 105° C.

EXAMPLE 3

Synthesis of (S)-1-{4'-[2-(2-benzoylphenylamino)-2-(5-propyl[1,3,4]oxadiazol-2-yl)ethyl]biphenyl-3-yl}-3-heptyl-1-methylurea 0.2 ml (1.8 mmol) of 4-methylmorpholine and 0.22 ml (1.7 mmol) of isobutyl chloroformate are added, at 0° C., to a solution containing 0.35 g (0.6 mmol) of (S)-2-(2-benzoylphenylamino)-3-[3'-(3-heptyl-1-methylureido)biphenyl-4-yl]propionic acid (Example 2) in 5 ml of tetrahydrofuran. After a return to ambient temperature, the reaction medium is stirred for 18 h and then filtered and immediately added to 3 ml (3.0 mmol) of a 1 M hydrazine solution in tetrahydrofuran at 0° C. After a return to ambient temperature, the mixture is stirred for 5 h and then treated with a saturated ammonium chloride solution, extracted with ethyl acetate, dried over magnesium sulfate, and concentrated. The residue obtained is used in crude form in the following step (m=0.70 g).

0.3 ml (1.8 mmol) of trimethyl orthobutyrate and a drop of methanesulfonic acid are added to the above residue dissolved in 15 ml of dioxane. The medium is heated at 105° C. for 3 h and then treated with a saturated sodium bicarbonate solution, extracted with ethyl acetate, dried over magnesium sulfate, and concentrated. The residue obtained is purified by chromatography on a column of silica and eluted with a 1/1 heptane/ethyl acetate mixture. 50 mg of (S)-1-{4'-[2-(2-benzoylphenylamino)-2-(5-propyl[1,3,4]oxadiazol-2-yl)ethyl]biphenyl-3-yl}-3-heptyl-1-methylurea are isolated with a 13% yield.

$^1$H NMR (CDCl$_3$) 0.85 (t, J=8 Hz, 3H); 0.97 (t, J=8 Hz, 3H); 1.28-1.24 (unresolved peak, 8H); 1.42 (unresolved peak, 2H); 1.79 (unresolved peak, J=8 Hz, 2H); 2.79 (t, J=8 Hz, 3H); 3.18 (unresolved peak, J=8 Hz, 2H); 3.30 (s, 3H); 3.45 (d, J=4 Hz, 2H); 4.37 (unresolved peak, 1H); 5.22 (q, J=4 Hz, 1H); 6.64 (t, J=8 Hz, 1H); 6.92 (d, J=8 Hz, 1H); 7.62-7.22 (unresolved peak, 14H); 9.05 (unresolved peak, 1H)

EXAMPLE 4

Synthesis of ethyl (S)-2-(2-benzoylphenylamino)-3-{3'-[3-(4-dimethylaminophenyl)-1-methylureido]biphenyl-4-yl}propionate In a manner similar to the preparation of the ethyl (S)-2-(2-benzoylphenylamino)-3-[3'-(3-heptyl-1-methylureido)biphenyl-4-yl]propionate (Example 1h), using 1.0 g (2.1 mmol) of ethyl (S)-2-(2-benzoylphenylamino)-3-(3'-methylaminobiphenyl-4-yl)propionate (Example 1g) and 0.40 g (2.47 mmol) of 4-(diethylamino)phenyl isocyanate, 0.86 g of ethyl (S)-2-(2-benzoylphenylamino)-3-{3'-[3-(4-dimethylaminophenyl)-1-methylureido]biphenyl-4-yl}propionate is isolated with a 75% yield.

Melting point: 75° C.

EXAMPLE 5

Synthesis of (S)-2-(2-benzoylphenylamino)-3-{3'-[3-(4-dimethylaminophenyl)-1-methylureido]biphenyl-4-yl}propionic acid In a manner similar to the preparation of the (S)-2-(2-benzoylphenylamino)-3-[3'-(3-heptyl-1-methylureido)biphenyl-4-yl]propionic acid (Example 2), using 0.60 g (0.9 mmol) of ethyl (S)-2-(2-benzoylphenylamino)-3-{3'-[3-(4-dimethylaminophenyl)-1-methylureido]biphenyl-4-yl}propionate (Example 4) and 43 mg (1.02 mmol) of lithium hydroxide, 0.41 g of (S)-2-(2-benzoylphenylamino)-3-{3'-[3-(4-dimethylaminophenyl)-1-methylureido]biphenyl-4-yl}propionic acid is obtained with an 89% yield.

Melting point: 130° C.

EXAMPLE 6

Synthesis of (S)-2-(2-benzoylphenylamino)-3-[3'-(1-methyl-3-naphthalen-2-yl ureido)biphenyl-4-yl]propionic acid a. Preparation of ethyl (S)-2-(2-benzoylphenylamino)-3-[3'-(1-methyl-3-naphthalen-2-ylureido)biphenyl-4-yl]propionate In a manner similar to the preparation of the ethyl (S)-2-(2-benzoylphenylamino)-3-[3'-(3-heptyl-1-methylureido)biphenyl-4-yl]propionate (Example 1h), using 0.54 g (1.13 mmol) of ethyl (S)-2-(2-benzoylphenylamino)-3-(3'-methylaminobiphenyl-4-yl)propionate (Example 1g) and 0.23 g (1.36 mmol) of 2-naphthylisocyanate, 0.66 g of expected urea is isolated with a 91% yield.

b. Synthesis of (S)-2-(2-benzoylphenylamino)-3-[3'-(1-methyl-3-naphthalen-2-ylureido)biphenyl-4-yl]propionic acid In a manner similar to the preparation of the (S)-2-(2-benzoylphenylamino)-3-[3'-(3-heptyl-1-methylureido)biphenyl-4-yl]propionic acid (Example 2), using 0.66 g (1.02 mmol) of ethyl (S)-2-(2-benzoylphenylamino)-3-[3'-(1-methyl-3-naphthalen-2-ylureido)biphenyl-4-yl]propionate and 50 mg (1.19 mmol) of lithium hydroxide, 0.61 g of (S)-2-(2-benzoylphenylamino)-3-[3'-(1-methyl-3-naphthalen-2-ylureido)biphenyl-4-yl]propionic acid is obtained with a 96% yield.

Melting point: 125° C.

EXAMPLE 7

Synthesis of isobutyl (S)-{4'-[2-(2-benzoylphenylamino)-2-(5-propyl[1,3,4]oxadiazol-2-yl)ethyl]biphenyl-3-yl}methylcarbamate a. Preparation of (S)-2-(2-benzoylphenylamino)-3-(3'-methylaminobiphenyl-4-yl)propionic acid In a manner similar to the preparation of the (S)-2-(2-benzoylphenylamino)-3-[3'-(3-heptyl-1-methylureido)biphenyl-4-yl]propionic acid (Example 2), using 1.2 g (1.06 mmol) of ethyl (S)-2-(2-benzoylphenyl-amino)-3-(3'-methylaminobiphenyl-4-yl)propionate (Example 1g) and 120 mg (2.85 mmol) of lithium hydroxide, 0.90 g of acid is obtained with an 80% yield.

b. Synthesis of isobutyl (S)-{4'-[2-(2-benzoylphenylamino)-2-(5-propyl[1,3,4]oxadiazol-2-yl)ethyl]biphenyl-3-yl}methylcarbamate In a manner similar to the preparation of the (S)-1-{4'-[2-(2-benzoylphenylamino)-2-(5-propyl[1,3,4]oxadiazol-2-yl)ethyl]biphenyl-3-yl}-3-heptyl-1-methylurea (Example 3), using 0.90 g (2.0 mmol) of (S)-2-(2-benzoylphenylamino)-3-(3'-methylaminobiphenyl-4-yl)propionic acid, 0.30 g of isobutyl (S)-{4'-[2-(2-benzoylphenylamino)-2-(5-propyl[1,3,4]oxadiazol-2-yl)ethyl]biphenyl-3-yl}methylcarbamate is isolated with a 37% yield.

Thermoquest Hypersil HPLC, Hypurity Elite C18, 3 microns, 2.1×150 mm, mobile phase: A (CH$_3$CN/0.1 v/v HCO$_2$H); B(H$_2$O/0.1 v/v HCO$_2$H), flow rate: 0.5 ml/min, gradient: 0 min: 35% B, 25.0 min: 5% B, 30.0 min: 5% B retention time: 21.0 min, purity: 92%, MS (ESI) m/z 617.3 (M+H)$^+$

EXAMPLE 8

Synthesis of (S)-2-(2-benzoylphenylamino)-3-[3'-(3-heptyl-1-methylureido)biphenyl-4-yl]-N-pentylpropionamide A solution of 19 mg (50.0 μmol) of HATU in 0.2 ml of DMF, 49 mg (68.0 μmol) of PS-carbodiimide resin and 2.7 mg (31.0 μmol) of N-amylamine in 0.4 ml of DCM are added successively to a solution containing 20 mg (33.8 μmol) of (S)-2-(2-benzoylphenylamino)-3-[3'-(3-heptyl-1-methylureido)biphenyl-4-yl]propionic acid (Example 2) in 0.2 ml of DMF. After stirring for 4 h, the reaction medium is filtered and the solvents are evaporated off. The reaction crude is dissolved in 0.5 ml of a 4/1 DCM/DMF mixture and 62 mg (170 μmol) of MP-carbonate resin are added. After stirring for 5 h, the resin is filtered off and the solvents are evaporated off. 22 mg of (S)-2-(2-benzoylphenylamino)-3-[3'-(3-heptyl-1-methylureido)biphenyl-4-yl]-N-pentylpropionamide are obtained with a quantitative yield.

Thermoquest Hypersil HPLC, Hypurity Elite C18, 3 microns, 2.1×150 mm, (CH$_3$CN/HCO$_2$H/H$_2$O: 5/0.01/5), flow rate: 0.5 ml/min, retention time: 18.1 min, purity: 93%, ESMS m/z 661.2 (M+H)$^+$

EXAMPLE 9

Synthesis of (S)-1-{4'-[2-(2-benzoylphenylamino)-3-(4-methylpiperid-1-yl)-3-oxopropyl]biphenyl-3-yl}-3-heptyl-1-methylurea In a similar manner, using 20 mg (33.8 μmol) of the (S)-2-(2-benzoylphenylamino)-3-[3'-(3-heptyl-1-methylureido)biphenyl-4-yl]propionic acid (Example 2) and 3.0 mg (30.2 μmol) of 4-methylpiperidine, 23 mg of (S)-1-{4'-[2-(2-benzoyl phenylamino)-3-(4-methylpiperid-1-yl)-3-oxopropyl]biphenyl-3-yl}-3-heptyl-1-methylurea are obtained with a quantitative yield.

Thermoquest Hypersil HPLC, Hypurity Elite C18, 3 microns, 2.1×150 mm, (CH$_3$CN/HCO$_2$H/H$_2$O: 5/0.01/5), flow rate: 0.5 ml/min, retention time: 18.1 min, purity: 93%, ESMS m/z 673.2 (M+H)$^+$

EXAMPLE 10

Synthesis of (S)—N-(2-acetylaminoethyl)-2-(2-benzoylphenylamino)-3-[3'-(3-heptyl-1-methylureido)biphenyl-4-yl]propionamide In a similar manner, using 20 mg (33.8 μmol) of the (S)-2-(2-benzoylphenylamino)-3-[3'-(3-heptyl-1-methylureido)biphenyl-4-yl]propionic acid (Example 2) and 3.1 mg (30.4 μmol) of N-acetylethylamine, 21 mg of (S)—N-(2-acetylaminoethyl)-2-(2-benzoylphenylamino)-3-[3'-(3-heptyl-1-methylureido)biphenyl-4-yl]propionamide are obtained with a 92% yield.

Thermoquest Hypersil HPLC, Hypurity Elite C18, 3 microns, 2.1×150 mm, (CH$_3$CN/HCO$_2$H/H$_2$O: 5/0.01/5), flow rate: 0.5 ml/min, retention time: 7.46 min, purity: 83%, ESMS m/z 676.0 (M+H)$^+$

EXAMPLE 11

Synthesis of (S)-2-(2-benzoylphenylamino)-N-benzyl-3-[3'-(3-heptyl-1-methylureido)biphenyl-4-yl]propionamide In a similar manner, using 20 mg (33.8 μmol) of the (S)-2-(2-benzoylphenylamino)-3-[3'-(3-heptyl-1-methylureido)biphenyl-4-yl]propionic acid (Example 2) and 3.3 mg (30.8 μmol) of benzylamine, 21 mg of (S)-2-(2-benzoylphenylamino)-N-benzyl-3-[3'-(3-heptyl-1-methylureido)biphenyl-4-yl]propionamide are obtained with a 93% yield.

Thermoquest Hypersil HPLC, Hypurity Elite C18, 3 microns, 2.1×150 mm, (CH$_3$CN/HCO$_2$H/H$_2$O: 5/0.01/5), flow rate: 0.5 ml/min, retention time: 15.3 min, purity: 85%, ESMS m/z 681.0 (M+H)$^+$

EXAMPLE 12

Synthesis of (S)-1-{2-(2-benzoylphenylamino)-3-[3'-(3-heptyl-1-methylureido)biphenyl-4-yl]propionyl}piperidine-4-carboxylic acid ethyl ester In a similar manner, using 20 mg (33.8 μmol) of the (S)-2-(2-benzoylphenylamino)-3-[3'-(3-heptyl-1-methylureido)biphenyl-4-yl]propionic acid (Example 2) and 4.8 mg (30.5 μmol) of ethyl piperidine-4-carboxylate, 24 mg of expected product are obtained with a quantitative yield.

Thermoquest Hypersil HPLC, Hypurity Elite C18, 3 microns, 2.1×150 mm, (CH$_3$CN/HCO$_2$H/H$_2$O: 5/0.01/5), flow rate: 0.5 ml/min, retention time: 16.2 min, purity: 84%, ESMS m/z 730.7 (M+H)$^+$

EXAMPLE 13

Synthesis of (S)-2-(2-benzoylphenylamino)-N,N-dibenzyl-3-[3'-(3-heptyl-1-methylureido)biphenyl-4-yl]propionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 6.0 mg (30.5 µmol) of dibenzylamine, 23 mg of (S)-1-{4'-[2-(2-benzoylphenylamino)-3-morpholin-4-yl-3-oxopropyl]biphenyl-3-yl}-3-heptyl-1-methylurea are obtained with an 87% yield.

Thermoquest Hypersil HPLC, Hypurity Elite C18, 3 microns, 2.1×150 mm, ($CH_3CN/HCO_2H/H_2O$: 5/0.01/5), flow rate: 0.5 ml/min, retention time: 21.3 min, purity: 77%, ESMS m/z 770.5 $(M+H)^+$

EXAMPLE 14

Synthesis of (S)-1-{4'-[2-(2-benzoylphenylamino)-3-morpholin-4-yl-3-oxopropyl]biphenyl-3-yl}-3-heptyl-1-methylurea In a similar manner, using 20 mg (33.8 µmol) of the (S)-2-(2-benzoylphenylamino)-3-[3'-(3-heptyl-1-methylureido)biphenyl-4-yl]propionic acid (Example 2) and 2.7 mg (31.0 µmol) of morpholine, 20 mg of (S)-1-{4'-[2-(2-benzoylphenylamino)-3-morpholin-4-yl-3-oxopropyl]biphenyl-3-yl}-3-heptyl-1-methylurea are obtained with a 91% yield.

Waters Symmetry Shield RP8 HPLC, 3 microns, 2.1×150 mm, ($CH_3CN/HCO_2H/H_2O$: 5/0.01/5), flow rate: 0.35 ml/min, retention time: 5.49 min, purity: 94%, ESMS m/z 661.3 $(M+H)^+$

EXAMPLE 15

Synthesis of (S)-2-(2-benzoylphenylamino)-3-[3'-(3-heptyl-1-methylureido)biphenyl-4-yl]-N-(3-methylbutyl)propionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 2.7 mg (31.0 µmol) of isoamylamine, 20 mg of (S)-2-(2-benzoylphenylamino)-3-[3'-(3-heptyl-1-methylureido)biphenyl-4-yl]-N-(3-methylbutyl)propionamide are obtained with a 92% yield.

Waters Symmetry Shield RP8 HPLC, 3 microns, 2.1×150 mm, ($CH_3CN/HCO_2H/H_2O$: 5/0.01/5), flow rate: 0.35 ml/min, retention time: 6.83 min, purity: 80%, ESMS m/z 661.4 $(M+H)^+$

EXAMPLE 16

Synthesis of (S)-1-{4'-[2-(2-benzoylphenylamino)-3-(4-methylpiperazin-1-yl)-3-oxopropyl]biphenyl-3-yl}-3-heptyl-1-methylurea In a similar manner, using 20 mg (33.8 µmol) of the (S)-2-(2-benzoylphenylamino)-3-[3'-(3-heptyl-1-methylureido)biphenyl-4-yl]propionic acid (Example 2) and 3.0 mg (29.9 µmol) of 1-methylpiperazine, 20 mg of (S)-1-{4'-[2-(2-benzoylphenylamino)-3-(4-methylpiperazin-1-yl)-3-oxopropyl]biphenyl-3-yl}-3-heptyl-1-methylurea are obtained with an 89% yield.

Waters Symmetry Shield RP8 HPLC, 3 microns, 2.1×150 mm, ($CH_3CN/HCO_2H/H_2O$: 5/0.01/5), flow rate: 0.35 ml/min, retention time: 2.14 min, purity: 88%, ESMS m/z 674.4 $(M+H)^+$

EXAMPLE 17

Synthesis of (S)-2-(2-benzoylphenylamino)-3-[3'-(3-heptyl-1-methylureido)biphenyl-4-yl]-N-hexylpropionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 3.1 mg (30.6 µmol) of N-hexylamine, 19 mg of (S)-2-(2-benzoylphenylamino)-3-[3'-(3-heptyl-1-methylureido)biphenyl-4-yl]-N-hexylpropionamide are obtained with an 85% yield.

Waters Symmetry Shield RP8 HPLC, 3 microns, 2.1×150 mm, ($CH_3CN/HCO_2H/H_2O$: 5/0.01/5), flow rate: 0.35 ml/min, retention time: 7.51 min, purity: 94%, ESMS m/z 675.4 $(M+H)^+$

EXAMPLE 18

Synthesis of (S)-2-(2-benzoylphenylamino)-3-[3'-(3-heptyl-1-methylureido)biphenyl-4-yl]-N-pyridin-2-ylmethylpropionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 3.3 mg (30.5 µmol) of 2-(aminomethyl)pyridine, 22 mg of (S)-2-(2-benzoylphenylamino)-3-[3'-(3-heptyl-1-methylureido)biphenyl-4-yl]-N-pyridin-2-ylmethylpropionamide are obtained with a 94% yield.

Waters Symmetry Shield RP8 HPLC, 3 microns, 2.1×150 mm, ($CH_3CN/HCO_2H/H_2O$: 5/0.01/5), flow rate: 0.35 ml/min, retention time: 3.96 min, purity: 93%, ESMS m/z 682.4 $(M+H)^+$

EXAMPLE 19

Synthesis of (S)-1-{4'-[2-(2-benzoylphenylamino)-3-2,6-dimethylmorpholin-4-yl)-3-oxopropyl]biphenyl-3-yl}-3-heptyl-1-methylurea In a similar manner, using 20 mg (33.8 µmol) of the (S)-2-(2-benzoylphenylamino)-3-[3'-(3-heptyl-1-methylureido)biphenyl-4-yl]propionic acid (Example 2) and 3.5 mg (30.4 µmol) of 2,6-dimethylmorpholine, 24 mg of (S)-1-{4'-[2-(2-benzoylphenylamino)-3-(2,6-dimethylmorpholin-4-yl)-3-oxopropyl]biphenyl-3-yl}-3-heptyl-1-methylurea are obtained with a quantitative yield.

Waters Symmetry Shield RP8 HPLC, 3 microns, 2.1×150 mm, ($CH_3CN/HCO_2H/H_2O$: 5/0.01/5), flow rate: 0.35 ml/min, retention time: 6.13 min and 6.45 min, purity: 21 and 70%, ESMS m/z 689.4 $(M+H)^+$

EXAMPLE 20

Synthesis of (S)-2-(2-benzoylphenylamino)-N-benzyl-3-[3'-(3-heptyl-1-methylureido)biphenyl-4-yl]-N-methyl-propionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 3.7 mg (30.5 µmol) of N-methylbenzylamine, 19 mg of (S)-2-(2-benzoylphenylamino)-N-benzyl-3-[3'-(3-heptyl-1-methylureido)biphenyl-4-yl]-N-methylpropionamide are obtained with an 80% yield.

Waters Symmetry Shield RP8 HPLC, 3 microns, 2.1×150 mm, (CH$_3$CN/HCO$_2$H/H$_2$O: 5/0.01/5), flow rate: 0.35 ml/min, retention time: 7.25 min, purity: 89%, ESMS m/z 695.4 (M+H)$^+$

EXAMPLE 21

Synthesis of (S)-2-(2-benzoylphenylamino)-3-[3'-(3-heptyl-1-methylureido)biphenyl-4-yl]-N-phenethyl-propionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 3.7 mg (30.5 µmol) of phenethylamine, 15 mg of (S)-2-(2-benzoylphenylamino)-3-[3'-(3-heptyl-1-methylureido)biphenyl-4-yl]-N-phenethylpropionamide are obtained with a 66% yield.

Waters Symmetry Shield RP8 HPLC, 3 microns, 2.1×150 mm, (CH$_3$CN/HCO$_2$H/H$_2$O: 5/0.01/5), flow rate: 0.35 ml/min, retention time: 6.67 min, purity: 94%, ESMS m/z 695.4 (M+H)$^+$

EXAMPLE 22

Synthesis of (S)-2-(2-benzoylphenylamino)-3-[3'-(3-heptyl-1-methylureido)biphenyl-4-yl]-N-[3-(2-oxo-1-pyrrolidinyl)propyl]propionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 4.3 mg (30.2 µmol) of 1-(3-aminopropyl)-2-pyrrolidinone, 22 mg of (S)-2-(2-benzoylphenylamino)-3-[3'-(3-heptyl-1-methylureido)biphenyl-4-yl]-N-[3-(2-oxo-1-pyrrolidinyl)propyl]propionamide are obtained with a 90% yield.

Waters Symmetry Shield RP8 HPLC, 3 microns, 2.1×150 mm, (CH$_3$CN/HCO$_2$H/H$_2$O: 5/0.01/5), flow rate: 0.35 ml/min, retention time: 4.41 min, purity: 81%, ESMS m/z 716.4 (M+H)$^+$

EXAMPLE 23

Synthesis of (S)-2-(2-benzoylphenylamino)-N-(2,5-difluorobenzyl)-3-[3'-(3-heptyl-1-methylureido)biphenyl-4-yl]propionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 4.4 mg (30.7 µmol) of 2,5-difluorobenzylamine, 20 mg of (S)-2-(2-benzoylphenylamino)-N-(2,5-difluorobenzyl)-3-[3'-(3-heptyl-1-methylureido)biphenyl-4-yl]propionamide are obtained with an 82% yield.

Waters Symmetry Shield RP8 HPLC, 3 microns, 2.1×150 mm, (CH$_3$CN/HCO$_2$H/H$_2$O: 5/0.01/5), flow rate: 0.35 ml/min, retention time: 6.62 min, purity: 93%, ESMS m/z 717.3 (M+H)$^+$

EXAMPLE 24

Synthesis of tert-butyl (S)-4-{2-(2-benzoylphenylamino)-3-[3'-(3-heptyl-1-methylureido)biphenyl-4-yl]propionyl}piperazine-1-carboxylate In a similar manner, using 20 mg (33.8 µmol) of the (S)-2-(2-benzoylphenylamino)-3-[3'-(3-heptyl-1-methylureido)biphenyl-4-yl]propionic acid (Example 2) and 5.7 mg (30.6 µmol) of tert-butyl piperazine-1-carboxylate, 19 mg of tert-butyl (S)-4-{2-(2-benzoylphenylamino)-3-[3'-(3-heptyl-1-methylureido)biphenyl-4-yl]propionyl}piperazine-1-carboxylate are obtained with a 74% yield.

Waters Symmetry Shield RP8 HPLC, 3 microns, 2.1×150 mm, (CH$_3$CN/HCO$_2$H/H$_2$O: 5/0.01/5), flow rate: 0.35 ml/min, retention time: 7.09 min, purity: 91%, ESMS m/z 760.4 (M+H)$^+$

EXAMPLE 25

Synthesis of (S)-2-(2-benzoylphenylamino)-N-butyl-3-[3'-(3-heptyl-1-methylureido)biphenyl-4-yl]propionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 2.2 mg (30.1 µmol) of N-butylamine, 17 mg of (S)-2-(2-benzoylphenylamino)-N-butyl-3-[3'-(3-heptyl-1-methylureido)biphenyl-4-yl]propionamide are obtained with a 79% yield.

Waters Symmetry Shield RP8 HPLC, 3 microns, 2.1×150 mm, (CH$_3$CN/HCO$_2$H/H$_2$O: 2/0.01/8), flow rate: 0.35 ml/min, retention time: 9.26 min, purity: 83%, ESMS m/z 647.4 (M+H)$^+$

EXAMPLE 26

Synthesis of (S)-2-(2-benzoylphenylamino)-N-(2-dimethylaminoethyl)-3-[3'-(3-heptyl-1-methylureido)biphenyl-4-yl]propionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 2.7 mg (30.6 µmol) of N,N-dimethylethylenediamine, 21 mg of (S)-2-(2-benzoylphenylamino)-N-(2-dimethylaminoethyl)-3-[3'-(3-heptyl-1-methylureido)biphenyl-4-yl]propionamide are obtained with a 94% yield.

Waters Symmetry Shield RP8 HPLC, 3 microns, 2.1×150 mm, (CH$_3$CN/HCO$_2$H/H$_2$O: 2/0.01/8), flow rate: 0.35 ml/min, retention time: 6.32 min, purity: 81%, ESMS m/z 662.4 (M+H)$^+$

EXAMPLE 27

Synthesis of (S)-2-(2-benzoylphenylamino)-3-[3'-(3-heptyl-1-methylureido)biphenyl-4-yl]-N-methyl-N-phenethylpropionamide In a similar manner, using 20 mg (33.8 µmol) of the (S)-2-(2-benzoylphenylamino)-3-[3'-(3-heptyl-1-methylureido)biphenyl-4-yl]propionic acid (Example 2) and 4.1 mg (30.3 µmol) of N-methylphenethylamine, 16 mg of (S)-2-(2-benzoylphenylamino)-3-[3'-(3-heptyl-1-methylureido)biphenyl-4-yl]-N-methyl-N-phenethylpropionamide are obtained with a 69% yield.

Waters Symmetry Shield RP8 HPLC, 3 microns, 2.1×150 mm, (CH$_3$CN/HCO$_2$H/H$_2$O: 2/0.01/8), flow rate: 0.35 ml/min, retention time: 9.98 min, purity: 91%, ESMS m/z 709.4 (M+H)$^+$

EXAMPLE 28

Synthesis of ethyl (S)-3-{3'-[(benzoylmethylamino)methyl]biphenyl-4-yl}-2-(2-benzoylphenylamino)-propionate a. Preparation of 2-(3-bromophenyl)[1,3]dioxolane 870 g (4.56 mol) of 3-bromobenzaldehyde, 2.6 l (45.6 mol) of 1,2-ethanediol, and 87 g (0.46 mol) of p-toluenesulfonic acid are dissolved in 4 l of toluene. After refluxing for 5 h 30, 1 l of an aqueous 1N sodium hydroxide solution is added at ambient temperature. The mixture obtained is filtered through celite, and the organic phase is recovered and washed with 2 l of water. The solvents are evaporated off and 1 060 g of acetal are obtained with a quantitative yield.

b. Preparation of 3-boronic acid-benzaldehyde

In a manner similar to the preparation of tert-butyl (3-boronic acid-phenyl)methylcarbamate (Example 1d), using 819 g (3.57 mol) of 2-(3-bromophenyl)[1,3]dioxolane, 355 g of crude product is used without purification in the following step.

c. Preparation of ethyl (S)-2-tert-butoxycarbonylamino-3-(3'-formylbiphenyl-4-yl)propionate In a manner similar to the preparation of ethyl (S)-2-tert-butoxycarbonylamino-3-[3'-(tert-butoxycarbonylmethylamino)biphenyl-4-yl]propionate (Example 1e), using 173 g (391 mmol) of ethyl (S)-2-tert-butoxycarbonylamino-3-(4-trifluoromethanesulfonyloxyphenyl)propionate and 82 g (547 mmol) of 3-boronic acid-benzaldehyde, 95.7 g of coupled product are isolated with a 61% yield.

d. Preparation of ethyl (S)-2-tert-butoxycarbonylamino-3-(3'-methylaminomethylbiphenyl-4-yl)propionate 21.2 g (314 mmol) of methylamine hydrochloride are introduced into a solution containing 25 g (63.0 mmol) of ethyl (S)-2-tert-butoxycarbonylamino-3-(3'-formylbiphenyl-4-yl)propionate in 200 ml of methanol. After stirring for 30 min at ambient temperature, 6.0 g (95.4 mmol) of sodium cyanoborohydride are added portionwise. The reaction medium is stirred for 16 h and the solvents are evaporated off. The residue is dissolved in ethyl acetate, and the organic phase is washed with water and then dried over magnesium sulfate and concentrated.

The crude product is purified by chromatography on a column of silica and eluted with a heptane/ethyl acetate and then a methanol/ethyl acetate mixture. 10 g of the expected amine are isolated with a 38% yield.

e. Preparation of ethyl (S)-3-{3'-[(benzoylmethylamino)methyl]biphenyl-4-yl}-2-tert-butoxycarbonylaminopropionate 4.2 ml (36.3 mmol) of benzoyl chloride are added to a solution containing 10 g (24.3 mmol) of ethyl (S)-2-tert-butoxycarbonylamino-3-(3'-methylaminomethylbiphenyl-4-yl)propionate and 10.1 ml (72.6 mmol) of triethylamine in 100 ml of tetrahydrofuran. The medium is stirred for 3 h and then hydrolysed, extracted with ethyl acetate, dried over magnesium sulfate, and concentrated. The residue obtained is purified by chromatography on a column of silica and eluted with a 3/2 heptane/ethyl acetate mixture. 8.0 g of expected amide are obtained with a 64% yield.

f. Preparation of ethyl (S)-2-amino-3-{3'-[(benzoylmethylamino)methyl]biphenyl-4-yl}propionate 8.0 g (15.5 mmol) of ethyl (S)-3-{3'-[(benzoylmethylamino)methyl]biphenyl-4-yl}-2-tert-butoxycarbonylaminopropionate are dissolved in 70 ml of dichloromethane. 12 ml (157 mmol) of trifluoroacetic acid are added in small amounts. The medium is stirred for 16 h and then brought to pH 9 with sodium carbonate, extracted with dichloromethane, dried over magnesium sulfate, and concentrated. The residue obtained is purified by chromatography on a column of silica and eluted with a 1/1 heptane/ethyl acetate mixture. 5.2 g of expected amine are obtained with an 82% yield.

g. Synthesis of ethyl (S)-3-{3'-[(benzoylmethylamino)methyl]-biphenyl-4-yl}-2-(2-benzoyl phenylamino)propionate In a manner similar to the preparation of the ethyl (S)-2-(2-benzoylphenylamino)-3-(3'-methylaminobiphenyl-4-yl)propionate (Example 1g), using 3.8 g (9.13 mmol) of ethyl (S)-2-amino-3-{3'-[(benzoylmethylamino)methyl]biphenyl-4-yl}propionate, 1.3 g of ethyl (S)-3-{3'-[(benzoylmethylamino)methyl]biphenyl-4-yl}-2-(2-benzoylphenylamino)propionate are isolated with a 24% yield.

Melting point: 55° C.

EXAMPLE 29

Synthesis of (S)-3-{3'-[(benzoylmethylamino)methyl]biphenyl-4-yl}-2-(2-benzoylphenylamino)propionic acid In a manner similar to the preparation of the (S)-2-(2-benzoylphenylamino)-3-[3'-(3-heptyl-1-methylureido)biphenyl-4-yl]propionic acid (Example 2), using 0.63 g (1.06 mmol) of ethyl (S)-3-{3'-[(benzoylmethylamino)methyl]biphenyl-4-yl}-2-(2-benzoylphenylamino)-propionate (Example 28g) and 55 mg (1.04 mmol) of lithium hydroxide, 0.45 g of (S)-3-{3'-[(benzoylmethylamino)methyl]biphenyl-4-yl}-2-(2-benzoylphenylamino)propionic acid is obtained with a 75% yield.

Melting point: 90° C.

EXAMPLE 30

Synthesis of (S)—N-{4'-[2-(2-benzoylphenylamino)-2-(5-propyl[1,3,4]oxadiazol-2-yl)ethyl]biphenyl-3-ylmethyl}-N-methylbenzamide In a manner similar to the preparation of (S)-1-{4'-[2-(2-benzoylphenylamino)-2-(5-propyl[1,3,4]oxadiazol-2-yl)ethyl]biphenyl-3-yl}-3-heptyl-1-methylurea (Example 3), using 0.65 g (1.14 mmol) of (S)-3-{3'-[(benzoylmethylamino)methyl]biphenyl-4-yl}-2-(2-benzoylphenylamino)propionic acid (Example 29), 0.13 g of (S)—N-{4'-[2-(2-benzoylphenylamino)-2-(5-propyl[1,3,4]oxadiazol-2-yl)ethyl]biphenyl-3-ylmethyl}-N-methylbenzamide is isolated with an 18% yield.

Melting point: 65° C.

$^1$H NMR (CDCl$_3$) 0.95 (t, J=8 Hz, 3H); 1.75 (unresolved peak, J=8H 2H); 2.77 (unresolved peak, J=8 Hz, 2H); 3.06-2.88 (unresolved peak, 3H); 3.43 (d, J=8 Hz, 2H); 4.80-4.55

(unresolved peak, 2H); 5.20 (unresolved peak, J=8 Hz, 2H); 6.61 (t, J=8 Hz, 1H); 6.90 (d, J=8 Hz, 1H); 7.61-7.125 (unresolved peak, 19H); 9.05 (d, J=8 Hz, 1H)

EXAMPLE 31

Synthesis of (S)-3-{3'-[benzoylmethylamino)methyl]biphenyl-4-yl}-2-(1-methyl-3-oxo-3-phenylpropenylamino)propionic acid a. Preparation of methyl (S)-2-amino-3-{3'-[(benzoylmethylamino)methyl]biphenyl-4-yl}propionate This product is prepared in an identical manner to the corresponding ethyl ester (Example 28f) but using methyl (S)-2-tert-butoxycarbonylamino-3-(4-hydroxyphenyl)propionate as starting tyrosine.

b. Preparation of methyl (S)-3-{3'-[(benzoylmethylamino)methyl]biphenyl-4-yl}-2-(1-methyl-3-oxo-3-phenylpropenylamino)propionate To 0.65 g (1.62 mmol) of methyl (S)-2-amino-3-{3'-[(benzoylmethylamino)methyl]biphenyl-4-yl}propionate, 0.32 g (1.94 mmol) of benzoylacetone, 3 g of molecular sieve 4A are added to 15 ml of methanol. The reaction mixture is refluxed for 14 h and then filtered through Celite. After evaporation of the solvents, the residue is purified by chromatography on a column of silica and eluted with a 7/3 heptane/ethyl acetate mixture. 0.62 g of desired product is isolated with 70% yield.

c. Synthesis of (S)-3-{3'-[(benzoylmethylamino)methyl]biphenyl-4-yl}-2-(1-methyl-3-oxo-3-phenylpropenylamino)propionic acid 1.7 ml (1.70 mmol) of an aqueous 1M lithium hydroxide solution are added to a solution containing 620 mg (1.13 mmol) of methyl (S)-3-{3'-[(benzoylmethylamino)methyl]biphenyl-4-yl}-2-(1-methyl-3-oxo-3-phenylpropenylamino)propionate in 10 ml of a methanol/THF mixture (3/1). After stirring for 16 h, the medium is acidified with 1N hydrochloric acid until pH=4, extracted with ethyl acetate, dried over magnesium sulfate, and concentrated. The residue is purified by chromatography on a column of silica and eluted with a heptane/ethyl acetate mixture. 100 mg of (S)-3-{3'-[(benzoylmethylamino)methyl]biphenyl-4-yl}-2-(1-methyl-3-oxo-3-phenylpropenylamino)propionic acid are isolated with a 17% yield.

Thermoquest Hypersil HPLC, Hypurity Elite C18, 3 microns, 2.1×150 mm, (CH$_3$CN/HCO$_2$H/H$_2$O: 1/0.01/9), flow rate: 0.5 ml/min, retention time: 15.6 min, purity: 88%, ESMS m/z 533.3 (M+H)$^+$

EXAMPLE 32

Synthesis of ethyl (S)-2-(2-{3'-[(benzoylmethylamino)methyl]biphenyl-4-yl}-1-ethoxycarbonylethylamino)benzoate In a manner similar to the preparation of the ethyl (S)-2-(2-benzoylphenylamino)-3-(3'-methylaminobiphenyl-4-yl)propionate (Example 1g), using 6.7 g (16.1 mmol) of ethyl (S)-2-amino-3-{3'-[(benzoylmethylamino)methyl]biphenyl-4-yl}propionate (Example 28f) and 3 ml (19.3 mmol) of ethyl 2-oxocyclohexanecarboxylate, 0.90 g of ethyl (S)-2-(2-{3'-[(benzoylmethylamino)methyl]biphenyl-4-yl}-1-ethoxycarbonylethylamino)-benzoate is isolated with a 10% yield.

$^1$H NMR (CDCl$_3$) 1.17 (t, J=8 Hz, 3H); 1.29 (t, J=8 Hz, 3H); 3.00-2.82 (unresolved peak, 3H); 3.22-3.11 (unresolved peak, 2H); 4.10 (q, J=8 Hz, 2H); 4.25 (q, J=8 Hz, 2H); 4.28 (m, J=8 Hz, 1H); 4.74-4.49 (unresolved peak, 2H); 6.58-6.51 (unresolved peak, 2H); 7.43-7.07 (unresolved peak, 13H); 7.87-7.43 (unresolved peak, 1H); 8.20 (d, 1H)

EXAMPLE 33

Synthesis of (S)-2-(2-{3'-[(benzoylmethylamino)methyl]biphenyl-4-yl}-1-ethoxycarbonylethylamino)benzoic acid In a manner similar to the preparation of the (S)-2-(2-benzoylphenylamino)-3-[3'-(3-heptyl-1-methylureido)biphenyl-4-yl]propionic acid (Example 2), using 0.30 g (0.53 mmol) of ethyl (S)-2-(2-{3'-[(benzoyl-methylamino)methyl]biphenyl-4-yl}-1-ethoxycarbonylethylamino)benzoate (Example 32) and 20 mg (0.53 mmol) of lithium hydroxide, 80 mg of (S)-2-(2-{3'-[(benzoylmethylamino)methyl]biphenyl-4-yl}-1-ethoxycarbonyl-ethylamino)benzoic acid are obtained with a 34% yield.

Melting point: 70° C.
$^1$H NMR (CDCl$_3$) 1.27 (t, J=8 Hz, 3H); 2.98-2.80 (unresolved peak, 3H); 3.28-3.07 (unresolved peak, 2H); 4.23 (q, J=8 Hz, 2H); 4.32 (unresolved peak, 1H); 4.73-4.47 (unresolved peak, 2H); 6.58-6.51 (unresolved peak, 2H); 7.43-7.07 (unresolved peak, 13H); 7.87-7.84 (unresolved peak, 1H); 8.19 (unresolved peak, 1H)

EXAMPLE 34

Synthesis of (S)-2-(2-{3'-[(benzoylmethylamino)methyl]biphenyl-4-yl}-1-carboxyethylamino)benzoic acid In a manner similar to the preparation of the (S)-2-(2-benzoylphenylamino)-3-[3'-(3-heptyl-1-methylureido)biphenyl-4-yl]propionic acid (Example 2), using 300 mg (0.53 mmol) of ethyl (S)-2-(2-{3'-[(benzoyl-methylamino)methyl]biphenyl-4-yl}-1-ethoxycarbonylethylamino)benzoate (Example 32) and 300 mg (7.14 mmol) of lithium hydroxide, 200 mg of (S)-2-(2-{3'-[(benzoyl methylamino)methyl]biphenyl-4-yl}-1-carboxyethylamino)-benzoic acid are obtained with a 74% yield.

Melting point: 127° C.
$^1$H NMR (CDCl$_3$) 2.91-2.76 (unresolved peak, 3H); 3.16-3.04 (unresolved peak, 2H); 4.39-4.34 (unresolved peak, 2H); 4.75-4.59 (unresolved peak, 1H); 6.54-6.49 (unresolved peak, 2H); 7.46-6.98 (unresolved peak, 14H); 7.83 (d, J=8 Hz, 1H)

EXAMPLE 35

Synthesis of methyl (R)-3-{3'-[(benzoylmethylamino)methyl]biphenyl-4-yl}-2-(2-benzoylphenylamino)-propionate a. Preparation of methyl (R)-2-tert-butoxycarbonylamino-3-(4-trifluoromethanesulfonyloxyphenyl)propionate In a manner similar to the preparation of ethyl (S)-2-tert-butoxycarbonylamino-3-(4-trifluoromethanesulfonyloxyphenyl)propionate (Example 1b), using 25 g (84.7 mmol) of methyl (R)-2-tert-butoxy-carbonylamino-3-(4-hydroxyphenyl)propionate, 33 g of triflate are isolated with a 91% yield.

b. Preparation of methyl (R)-2-tert-butoxycarbonylamino-3-(3'-formylbiphenyl-4-yl)propionate 100 ml (201 mmol) of an aqueous 2M potassium carbonate solution and 4.4 g (3.80 mmol) of tetrakis palladium are introduced into a solution containing 33 g (77.3 mmol) of methyl (R)-2-tert-butoxycarbonylamino-3-(4-trifluoromethanesulfonyloxyphenyl)propionate, and 15 g (100 mmol) of 3-boronic acid-benzaldehyde (Example 28b) in 300 ml of ethylene glycol dimethyl ether. The reaction medium is heated at 85° C. for 20 h and, after a return to ambient temperature, extracted with ethyl acetate. The organic phase is washed with water and then a saturated sodium chloride solution, dried over magnesium sulfate, and concentrated. The residue obtained is purified by chromatography on a column of silica and eluted with a 7/3 heptane/ethyl acetate mixture. 10.2 g of coupled product are obtained with a 35% yield.

c. Preparation of methyl (R)-2-tert-butoxycarbonylamino-3-(3'-methylaminomethyl biphenyl-4-yl)propionate In a manner similar to the preparation of ethyl (S)-2-tert-butoxycarbonylamino-3-(3'-methylaminomethylbiphenyl-4-yl)propionate (Example 28d) using 10.2 g (26.6 mmol) of methyl (R)-2-tert-butoxycarbonyl-amino-3-(3'-formylbiphenyl-4-yl)propionate, 5.0 g of expected amine are isolated with a 50% yield.

d. Preparation of methyl (R)-3-{3'-[(benzoylmethylamino)methyl]biphenyl-4-yl}-2-tert-butoxycarbonylaminopropionate In a manner similar to the preparation of ethyl (S)-3-{3'-[(benzoylmethylamino)methyl]biphenyl-4-yl}-2-tert-butoxycarbonylaminopropionate (Example 28e), using 5.0 g of methyl (R)-2-tert-butoxycarbonylamino-3-(3'-methylaminomethylbiphenyl-4-yl)propionate, 5.6 g of desired amide are obtained with an 85% yield.

e. Preparation of methyl (R)-2-amino-3-{3'-[(benzoylmethylamino)methyl]biphenyl-4-yl}propionate In a manner similar to the preparation of ethyl (S)-2-amino-3-{3'-[(benzoylmethylamino)methyl]biphenyl-4-yl}propionate (Example 28f), using 5.6 g of methyl (R)-3-{3'-[(benzoylmethylamino)methyl]biphenyl-4-yl}-2-tert-butoxycarbonylaminopropionate, 4.1 g of amine are obtained with a 92% yield.

f. Synthesis of methyl (R)-3-{3'-[(benzoylmethylamino)methyl]biphenyl-4-yl}-2-(2-benzoylphenylamino)propionate In a manner similar to the preparation of ethyl (S)-2-(2-benzoylphenylamino)-3-(3'-methylaminobiphenyl-4-yl)propionate (Example 1g), using 4.1 g (10.2 mmol) of methyl (R)-2-amino-3-{3'-[(benzoyl-methylamino)methyl]biphenyl-4-yl}propionate, 0.16 g of methyl (R)-3-{3'-[(benzoylmethylamino)methyl]biphenyl-4-yl}-2-(2-benzoylphenylamino)propionate is obtained with a 3% yield.

Melting point: 75° C.

EXAMPLE 36

Synthesis of (R)-3-{3'-[(benzoylmethylamino)methyl]biphenyl-4-yl}-2-(2-benzoylphenylamino)propionic acid In a manner similar to the preparation of the (S)-2-(2-benzoylphenylamino)-3-[3'-(3-heptyl-1-methylureido)biphenyl-4-yl]propionic acid (Example 2), using 130 g (0.15 mmol) of methyl (R)-3-{3'-[(benzoylmethylamino)methyl]biphenyl-4-yl}-2-(2-benzoylphenylamino)-propionate (Example 35f), 80 mg of (R)-3-{3'-[(benzoylmethylamino)methyl]-biphenyl-4-yl}-2-(2-benzoylphenylamino)propionic acid are isolated with a 63% yield.

Melting point: 110° C.

EXAMPLE 37

Synthesis of 3-{3'-[(benzoylmethylamino)methyl]biphenyl-4-yl}-2-tert-butoxycarbonylaminopropionic acid a. Preparation of 3-(4-bromophenyl)-2-tert-butoxycarbonylaminopropionic acid 8.95 g (41.0 mmol) of tert-butoxycarbonyl anhydride are added, portionwise, to a solution containing 5.2 g (21.3 mmol) of 4-bromophenylalanine in 50 ml of a 9/1 methanol/triethylamine mixture. The reaction medium is heated at 50° C. for 30 min, and the solvents are evaporated off.

Ethyl acetate and water are added to the residue obtained. The aqueous phase is acidified to pH 2 with 1N hydrochloric acid and the organic phase is recovered, dried over magnesium sulfate and concentrated. 6.2 g of the expected amine are isolated with an 85% yield.

b. Preparation of benzyl 3-(4-bromophenyl)-2-tert-butoxycarbonylaminopropionate 2.4 ml (19.8 mmol) of benzyl bromide and 4.97 g (36 mmol) of potassium carbonate are added to a solution containing 6.2 g (18 mmol) of 3-(4-bromophenyl)-2-tert-butoxycarbonylaminopropionic acid in 75 ml of methylethyl ketone. The reaction medium is refluxed for 2 h 30, filtered and concentrated. The residue obtained is purified by chromatography on a column of silica and eluted with a 3/7 heptane/ethyl acetate mixture. 6.8 g of benzyl ester are isolated with an 87% yield.

c. Preparation of benzyl 2-tert-butoxycarbonylamino-3-(3'-formylbiphenyl-4-yl)propionate 23 ml (45.9 mmol) of an aqueous 2M potassium carbonate solution and 1.77 g (1.50 mmol) of tetrakis palladium are introduced into a solution containing 6.64 g (15.3 mmol) of benzyl 3-(4-bromophenyl)-2-tert-butoxycarbonylaminopropionate and 3.45 g (23 mmol) of 3-boronic acid-benzaldehyde (Example 28b) in 75 ml of toluene. The reaction medium is heated at 80° C. for 20 h and, after a return to ambient temperature, extracted with ethyl acetate. The organic phase is washed with a saturated sodium chloride solution, dried over magnesium sulfate and concentrated. The residue obtained is purified by chromatography on a column of silica and eluted with an 8/2 heptane/ethyl acetate mixture. 5.0 g of coupled product are obtained with a 71% yield.

d. Preparation of benzyl 2-tert-butoxycarbonylamino-3-(3'-methylaminomethylbiphenyl-4-yl)propionate In a manner similar to the preparation of ethyl (S)-2-tert-butoxycarbonylamino-3-(3'-methylaminomethylbiphenyl-4-yl)propionate (Example 28d), using 4.69 g (10.2 mmol) of benzyl 2-tert-butoxycarbonyl-amino-3-(3'-formylbiphenyl-4-yl)propionate, 2.7 g of expected methylamine are obtained with a 57% yield.

e. Preparation of benzyl 3-{3'-[(benzoylmethylamino)methyl]biphenyl-4-yl}-2-tert-butoxycarbonylaminopropionate In a manner similar to the preparation of ethyl (S)-3-{3'-[(benzoylmethylamino)methyl]biphenyl-4-yl}-2-tert-butoxycarbonylaminopropionate (Example 28e), using 2.62 g (5.67 mmol) of benzyl 2-tert-butoxycarbonylamino-3-(3'-methylaminomethylbiphenyl-4-yl)-propionate, 1.9 g of desired amide are isolated with a 60% yield.

f. Synthesis of 3-{3'-[(benzoylmethylamino)methyl]biphenyl-4-yl}-2-tert-butoxycarbonylaminopropionic acid 58 mg (10% by mass) of 10% palladium-on-charcoal are introduced into a solution containing 580 mg of benzyl 3-{3'-[(benzoylmethylamino)methyl]biphenyl-4-yl}-2-tert-butoxycarbonylaminopropionate in 8 ml of ethyl acetate. After bubbling hydrogen into the solution for 16 h at ambient temperature and 2 h at 50° C., the reaction medium is filtered through Celite and the solvents are evaporated off. The residue obtained is purified by chromatography on a column of silica and eluted with a 3/7 heptane/ethyl acetate mixture. 300 mg of 3-{3'-[(benzoylmethylamino)methyl]biphenyl-4-yl}-2-tert-butoxycarbonylaminopropionic acid are obtained with a 61% yield.

Melting point: 80° C.

EXAMPLE 38

Synthesis of 3-{3'-[(benzoylmethylamino)methyl]biphenyl-4-yl}-2-(1-methyl-3-oxo-3-phenylpropenylamino)propionic acid a. Preparation of methyl 3-{3'-[(benzoylmethylamino)methyl]biphenyl-4-yl}-2-(1-methyl-3-oxo-3-phenylpropenylamino)propionate In a manner similar to the preparation of the methyl (S)-3-{3'-[(benzoylmethylamino)methyl]biphenyl-4-yl}-2-(1-methyl-3-oxo-3-phenylpropenylamino)propionate (Example 31b), using 500 mg (1.24 mmol) of methyl 2-amino-3-{3'-[(benzoylmethylamino)methyl]biphenyl-4-yl}propionate, 450 mg of expected product is obtained with a 66% yield.

b. Synthesis of 3-{3'-[(benzoylmethylamino)methyl]biphenyl-4-yl}-2-(1-methyl-3-oxo-3-phenylpropenylamino)propionic acid In a manner similar to the preparation of the (S)-3-{3'-[(benzoylmethylamino)methyl]biphenyl-4-yl}-2-(1-methyl-3-oxo-3-phenylpropenylamino)propionic acid (Example 31c), using 438 mg (0.80 mmol) of 3-{3'-[(benzoylmethylamino)methyl]biphenyl-4-yl}-2-(1-methyl-3-oxo-3-phenylpropenylamino)propionate, 90 mg of 3-{3'-[(benzoylmethylamino)methyl]biphenyl-4-yl}-2-(1-methyl-3-oxo-3-phenylpropenylamino)propionic acid are isolated with a 22% yield.

Melting point: 136° C.

EXAMPLE 39

Synthesis of butyl (S)-2-(2-benzoylphenylamino)-3-[3'-(3-heptyl-1-methylureido)biphenyl-4-yl]propionate 4.7 mg (63.3 µmol) of n-butanol, 5.7 mg (8.5 µmol) of PS-DMAP resin and 68 mg (94.0 µmol) of PS-carbodiimide are added successively to a solution containing 25 mg (42.3 µmol) of (S)-2-(2-benzoylphenylamino)-3-[3'-(3-heptyl-1-methylureido)biphenyl-4-yl]propionic acid (Example 2) in 0.6 ml of DCM. After stirring for 16 h at ambient temperature and then 5 h at 40° C., the reaction medium is filtered and the solvents are evaporated off. The reaction crude is purified by chromatography on a column of silica and eluted with a heptane/ethyl acetate mixture. 5.5 mg of butyl (S)-2-(2-benzoylphenylamino)-3-[3'-(3-heptyl-1-methylureido)biphenyl-4-yl]propionate are obtained with a 20% yield.

HPLC: Thermohypersil Hypurity C18 column, 3 microns, 2.1×30 mm, Mobile phase: A(CH$_3$CN/0.1 v/v HCO$_2$H); B (H$_2$O/0.1 v/v HCO$_2$H), Flow rate: 0.35 ml/min, gradient: 0 min: 35% A, 3.0 min: 5% A, 5.0 min: 5% A Retention time: 4.22 min, purity: 100%, MS (ESI) m/z 648.4 (M+H)$^+$

EXAMPLE 40

Synthesis of hexyl (S)-2-(2-benzoylphenylamino)-3-[3'-(3-heptyl-1-methylureido)biphenyl-4-yl]propionate In a similar manner, using 25 mg (42.3 µmol) of the (S)-2-(2-benzoylphenylamino)-3-[3'-(3-heptyl-1-methylureido)biphenyl-4-yl]propionic acid (Example 2) and 6.5 mg (63.6 µmol) of n-hexanol, 6.4 mg of hexyl (S)-2-(2-benzoylphenylamino)-3-[3'-(3-heptyl-1-methylureido)biphenyl-4-yl]propionate are obtained with a 22% yield.

HPLC: Thermohypersil Hypurity C18 column, 3 microns, 2.1×30 mm, Mobile phase: A(CH$_3$CN/0.1 v/v HCO$_2$H); B (H$_2$O/0.1 v/v HCO$_2$H), Flow rate: 0.35 ml/min, gradient: 0 min: 35% A, 3.0 min: 5% A, 5.0 min: 5% A Retention time: 4.46 min, purity: 100%, MS (ESI) m/z 676.4 (M+H)$^+$

EXAMPLE 41

Synthesis of benzyl (S)-2-(2-benzoylphenylamino)-3-[3'-(3-heptyl-1-methylureido)biphenyl-4-yl]propionate In a similar manner, using 25 mg (42.3 µmol) of the (S)-2-(2-benzoylphenylamino)-3-[3'-(3-heptyl-1-methylureido)biphenyl-4-yl]propionic acid (Example 2) and 6.9 mg (63.8 µmol) of benzyl alcohol, 3.4 mg of benzyl (S)-2-(2-benzoylphenylamino)-3-[3'-(3-heptyl-1-methylureido)biphenyl-4-yl]propionate are obtained with a 12% yield.

HPLC: Thermohypersil Hypurity C18 column, 3 microns, 2.1×30 mm, Mobile phase: A(CH$_3$CN/0.1 v/v HCO$_2$H); B (H$_2$O/0.1 v/v HCO$_2$H), Flow rate: 0.35 ml/min, gradient: 0 min: 35% A, 3.0 min: 5% A, 5.0 min: 5% A Retention time: 4.11 min, purity: 96%, MS (ESI) m/z 682.4 (M+H)$^+$

EXAMPLE 42

Synthesis of phenethyl (S)-2-(2-benzoylphenylamino)-3-[3'-(3-heptyl-1-methylureido)biphenyl-4-yl]propionate In a similar manner, using 25 mg (42.3 µmol) of the (S)-2-(2-benzoylphenylamino)-3-[3'-(3-heptyl-1-methylureido)biphenyl-4-yl]propionic acid (Example 2) and 7.8 mg (63.8 µmol) of phenethyl alcohol, 7.7 mg of phenethyl (S)-2-(2-benzoylphenylamino)-3-[3'-(3-heptyl-1-methylureido)biphenyl-4-yl]propionate are obtained with a 26% yield.

HPLC: Thermohypersil Hypurity C18 column, 3 microns, 2.1×30 mm, Mobile phase: A(CH$_3$CN/0.1 v/v HCO$_2$H); B (H$_2$O/0.1 v/v HCO$_2$H), Flow rate: 0.35 ml/min, gradient: 0 min: 35% A, 3.0 min: 5% A, 5.0 min: 5% A Retention time: 4.19 min, purity: 82%, MS (ESI) m/z 696.1 (M+H)$^+$

EXAMPLE 43

Synthesis of 2-ethylhexyl (S)-2-(2-benzoylphenylamino)-3-[3'-(3-heptyl-1-methylureido)biphenyl-4-yl]propionate In a similar manner, using 25 mg (42.3 µmol) of the (S)-2-(2-benzoylphenylamino)-3-[3'-(3-heptyl-1-methylureido)biphenyl-4-yl]propionic acid (Example 2) and 8.3 mg (63.7 µmol) of 2-ethylhexanol, 5.7 mg of 2-ethylhexyl (S)-2-(2-benzoylphenylamino)-3-[3'-(3-heptyl-1-methylureido)biphenyl-4-yl]propionate are obtained with a 19% yield.

HPLC: Thermohypersil Hypurity C18 column, 3 microns, 2.1×30 mm, Mobile phase: A(CH$_3$CN/0.1 v/v HCO$_2$H); B (H$_2$O/0.1 v/v HCO$_2$H), Flow rate: 0.5 ml/min, gradient: 0 min: 50% B, 20.0 min: 5% B, 30.0 min: 5% B Retention time: 19.3 min, purity: 98%, MS (ESI) m/z 704.5 (M+H)$^+$

EXAMPLE 44

Synthesis of 2-morpholin-4-ylethyl (S)-2-(2-benzoylphenylamino)-3-[3'-(3-heptyl-1-methylureido)biphenyl-4-yl]propionate In a similar manner, using 25 mg (42.3 µmol) of the (S)-2-(2-benzoylphenylamino)-3-[3'-(3-heptyl-1-methylureido)biphenyl-4-yl]propionic acid (Example 2) and 8.3 mg (63.3 µmol) of 2-morpholinoethanol, 3.8 mg of 2-morpholin-4-ylethyl (S)-2-(2-benzoylphenylamino)-3-[3'-(3-heptyl-1-methylureido)biphenyl-4-yl]propionate are obtained with a 13% yield.

HPLC: Thermohypersil Hypurity C18 column, 3 microns, 2.1×30 mm, mobile phase: A(CH$_3$CN/0.1 v/v HCO$_2$H); B (H$_2$O/0.1 v/v HCO$_2$H), low rate: 0.5 ml/min, gradient: 0 min: 50% B, 20.0 min: 5% B, 30.0 min: 5% B Retention time: 5.01 min, purity: 89%, MS (ESI) m/z 705.5 (M+H)$^+$

EXAMPLE 45

Synthesis of 3-methoxybenzyl (S)-2-(2-benzoylphenylamino)-3-[3'-(3-heptyl-1-methylureido)biphenyl-4-yl]-propionate In a similar manner, using 25 mg (42.3 µmol) of the (S)-2-(2-benzoylphenylamino)-3-[3'-(3-heptyl-1-methylureido)biphenyl-4-yl]propionic acid (Example 2) and 8.8 mg (63.7 µmol) of 2-methoxybenzyl alcohol, 10.3 mg of 3-methoxybenzyl (S)-2-(2-benzoylphenylamino)-3-[3'-(3-heptyl-1-methylureido)biphenyl-4-yl]propionate are obtained with a 34% yield.

HPLC: Thermohypersil Hypurity C18 column, 3 microns, 2.1×30 mm, Mobile phase: A(CH$_3$CN/0.1 v/v HCO$_2$H); B (H$_2$O/0.1 v/v HCO$_2$H), Flow rate: 0.5 ml/min, gradient: 0 min: 50% B, 20.0 min: 5% B, 30.0 min: 5% B Retention time: 14.7 min, purity: 89%, MS (ESI) m/z 712.3 (M+H)$^+$

EXAMPLE 46

Synthesis of 2-naphthylmethyl (S)-2-(2-benzoylphenylamino)-3-[3'-(3-heptyl-1-methylureido)biphenyl-4-yl]propionate In a similar manner, using 25 mg (42.3 µmol) of the (S)-2-(2-benzoylphenylamino)-3-[3'-(3-heptyl-1-methylureido)biphenyl-4-yl]propionic acid (Example 2) and 10.0 mg (63.2 µmol) of 2-naphthylmethanol, 18.6 mg of 2-naphthylmethyl (S)-2-(2-benzoylphenylamino)-3-[3'-(3-heptyl-1-methylureido)biphenyl-4-yl]propionate are obtained with a 60% yield.

HPLC: Thermohypersil Hypurity C18 column, 3 microns, 2.1×30 mm, Mobile phase: A(CH$_3$CN/0.1 v/v HCO$_2$H); B (H$_2$O/0.1 v/v HCO$_2$H), Flow rate: 0.5 ml/min, gradient: 0 min: 50% B, 20.0 min: 5% B, 30.0 min: 5% B Retention time: 16.5 min, purity: 96%, MS (ESI) m/z 732.3 (M+H)$^+$

EXAMPLE 47

Synthesis of 2-(5-methyl-2-phenyloxazol-4-yl)ethyl (S)-2-(2-benzoyl phenylamino)-3-[3'-(3-heptyl-1-methyl-ureido)biphenyl-4-yl]propionate In a similar manner, using 25 mg (42.3 µmol) of the (S)-2-(2-benzoylphenylamino)-3-[3'-(3-heptyl-1-methylureido)biphenyl-4-yl]propionic acid (Example 2) and 12.8 mg (63.5 µmol) of 2-(5-methyl-2-phenyloxazol-4-yl)ethanol, 5.0 mg of 2-(5-methyl-2-phenyloxazol-4-yl)ethyl (S)-2-(2-benzoylphenylamino)-3-[3'-(3-heptyl-1-methylureido)biphenyl-4-yl]propionate are obtained with a 15% yield.

HPLC: Thermohypersil Hypurity C18 column, 3 microns, 2.1×30 mm, Mobile phase: A(CH$_3$CN/0.1 v/v HCO$_2$H); B (H$_2$O/0.1 v/v HCO$_2$H), Flow rate: 0.5 ml/min, gradient: 0 min: 90% B, 25.0 min: 5% B, 30.0 min: 5% B Retention time: 24.2 min, purity: 100%, MS (ESI) m/z 777.3 (M+H)$^+$

EXAMPLE 48

Crossed-Curve PPAR Transactivation Assay

Activation of the receptors by an agonist (activator) in HeLN cells leads to the expression of a reporter gene, luciferase, which, in the presence of a substrate, generates light. The modulation of the receptors is measured by quantifying the luminescence produced after incubation of the cells in the presence of a reference agonist. The ligands will displace the agonist from its site. The measurement of the activity is performed by quantifying the light produced. This measurement makes it possible to determine the modulatory activity of the compounds according to the invention by determining the constant that is the affinity of the molecule for the receptor. Since this value can fluctuate depending on the basal activity and the expression of the receptor, it is referred to as Kd apparent (KdApp in nM).

To determine this constant, "crossed curves" for the test product, against a reference agonist, are prepared using a 96-well plate: 10 concentrations of the test product plus a concentration 0 are arranged in a line, and 7 concentrations of the agonist plus a concentration 0 are arranged in a column. This is 88 measurement points for 1 product and 1 receptor. The remaining 8 wells are used for repeatability controls.

In each well, the cells are in contact with a concentration of the test product and a concentration of the reference agonist, 2-(4-{2-[3-(2,4-difluoro-phenyl)-1-heptylureido] ethyl}phenylsulfanyl)-2-methylpropionic acid for PPARα, {2-methyl-4-[4-methyl-2-(4-trifluoromethylphenyl)thiazol-5-ylmethylsulfanyl]phenoxy}acetic acid for PPARδ and 5-{4-[2-(methylpyrid-2-ylamino)ethoxy] benzyl}thiazolidine-2,4-dione for PPARγ. Measurements are also taken for total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are seeded in 96-well plates at a rate of 10 000 cells per well in 100 µl of DMEM medium without phenol red and supplemented with 10% of defatted calf serum. The plates are then incubated for 16 hours at 37° C. and 7% CO$_2$.

The various dilutions of the test products and of the reference ligand are added at a rate of 5 µl per well. The plates are then incubated for 18 hours at 37° C. and 7% CO$_2$. The culture medium is removed by turning over and 100 µl of a 1:1 PBS/luciferin mixture are added to each well. After 5 minutes, the plates are read using the luminescence reader.

These crossed curves make it possible to determine the AC50 values (concentration at which 50% activation is observed) of the reference ligand at various concentrations of test product. These AC50 values are used to calculate the Schild regression by plotting a straight line corresponding to the Schild equation ("*quantitation in receptor pharmacology*" Terry P. Kenakin, *Receptors and Channels*, 2001, 7 371-385) which allows the Kd app values (in nM) to be obtained.

Transactivation results:

| Compounds | PPAR alpha Kd app (in nM) | PPAR delta Kd app (in nM) | PPAR gamma Kd app (in nM) |
|---|---|---|---|
| Reference 1: 2-(4-{2-[3-(2,4-difluoro-phenyl)-1-heptylureido]ethyl}phenyl-sulfanyl)-2-methylpropionic acid | 200 | n.a. | n.a. |
| Reference 2: {2-methyl-4-[4-methyl-2-(4-trifluoromethylphenyl)thiazol-5-ylmethylsulfanyl]phenoxy}acetic acid | n.a. | 10 | n.a. |
| Reference 3: 5-{4-[2-(methylpyrid-2-ylamino)ethoxy]benzyl}thiazolidine-2,4-dione | n.a. | n.a. | 30 |
| Example 3 | n.a. | n.a. | 30 |
| Example 6 | n.a. | n.a. | 4 |
| Example 8 | 2 000 | 500 | 30 |
| Example 9 | 2 000 | 1 000 | 30 |
| Example 10 | 2 000 | 1 000 | 60 |
| Example 13 | 8 000 | 1 000 | 8 |
| Example 16 | n.a. | n.a. | 30 |
| Example 18 | n.a. | 1 000 | 60 |
| Example 20 | 8 000 | n.a. | 30 |
| Example 26 | n.a. | n.a. | 60 |
| Example 27 | 4 000 | n.a. | 15 |
| Example 29 | 2 000 | n.a. | 500 |

-continued

| Compounds | PPAR alpha Kd app (in nM) | PPAR delta Kd app (in nM) | PPAR gamma Kd app (in nM) |
|---|---|---|---|
| Example 31 | 8 000 | n.a. | 15 |
| Example 39 | n.a. | n.a. | 30 | n.a. means not active

These results show the affinity of the compounds for PPAR-γ and more particularly the specificity of the affinity of the compounds of the invention for the PPARγ subtype, compared to the affinity of the compounds for the PPARα subtype or for the PPARδ subtype.

EXAMPLE 49

Compositions

Various specific formulations based on the compounds according to the invention are illustrated in this example.

A—Oral Route:

| (a) 0.2 g tablet: | |
|---|---|
| Compound 20 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

| (b) Oral suspension in 5 ml ampoules: | |
|---|---|
| Compound 8 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavoring | qs |
| Purified water | qs 5 ml |

| (c) 0.8 g tablet: | |
|---|---|
| Compound 9 | 0.500 g |
| Pregelatinized starch | 0.100 g |
| Microcrystalline cellulose | 0.115 g |
| Lactose | 0.075 g |
| Magnesium stearate | 0.010 g |

| (d) Oral suspension in 10 ml ampoules: | |
|---|---|
| Compound 10 | 0.200 g |
| Glycerol | 1.000 g |
| 70% sorbitol | 1.000 g |
| Sodium saccharinate | 0.010 g |
| Methyl para-hydroxybenzoate | 0.080 g |

37

-continued

| (d) Oral suspension in 10 ml ampoules: | |
|---|---|
| Flavoring | qs |
| Purified water | qs 10 ml |

B—Topical Route:

| (a) Ointment: | |
|---|---|
| Compound 13 | 0.020 g |
| Isopropyl myristate | 81.700 g |
| Liquid petroleum jelly fluid | 9.100 g |
| Silica ("Aerosil 200" sold by Degussa) | 9.180 g |

| (b) Ointment: | |
|---|---|
| Compound 16 | 0.300 g |
| White petroleum jelly codex | qs 100 g |

| (c) Nonionic water-in-oil cream: | |
|---|---|
| Compound 20 | 0.100 g |
| Mixture of emulsifying lanolin alcohols, waxes and oils ("Anhydrous Eucerin" sold by BDF) | 39.900 g |
| Methyl para-hydroxybenzoate | 0.075 g |
| Propyl para-hydroxybenzoate | 0.075 g |
| Sterile demineralized water | qs 100 g |

| (d) Lotion: | |
|---|---|
| Compound 27 | 0.100 g |
| Polyethylene glycol (PEG 400) | 69.900 g |
| 95% ethanol | 30.000 g |

| (e) Hydrophobic ointment: | |
|---|---|
| Compound 13 | 0.300 g |
| Isopropyl myristate | 36.400 g |
| Silicone oil ("Rhodorsil 47 V 300" sold by Rhône-Poulenc) | 36.400 g |
| Beeswax | 13.600 g |
| Silicone oil ("Abil 300 000 cst" sold by Goldschmidt) | qs 100 g |

| (f) Nonionic oil-in-water cream: | |
|---|---|
| Compound 6 | 1.000 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

38

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A biaromatic compound having the structural formula (I):

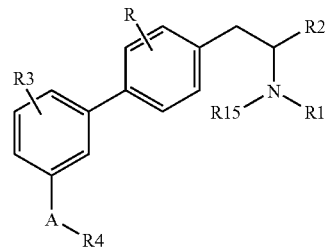

in which:
R is a halogen atom or a hydrogen atom;
$R_1$ is the radical

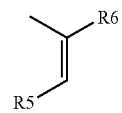

wherein $R_5$ and $R_6$ are as defined below;
$R_2$ is the radical:

wherein $R_9$ is as defined below;
$R_3$ is a hydrogen atom, a halogen atom, an alkyl radical having from 1 to 12 carbon atoms, a hydroxyl radical, an alkoxy radical having from 1 to 7 carbon atoms, a polyether radical, a nitro radical, or an amino radical that may optionally be substituted with one or more alkyl radicals having from 1 to 12 carbon atoms, an aryl radical, an aralkyl radical, a heteroaryl radical or a heterocyclic radical;
$R_4$ is an alkyl radical having from 1 to 12 carbon atoms, an aryl radical, an aralkyl radical, a heteroaryl radical, a heterocyclic radical or a 9-fluorenylmethyl radical;
$R_5$ is a hydrogen atom, an alkyl radical having from 1 to 12 carbon atoms, an alkoxy radical having from 1 to 7 carbon atoms, an aryl radical, an aralkyl radical, a heteroaryl radical, a heterocyclic radical or a group $(CO)_s(Z)_tR_7$, wherein Z, $R_7$, s and t are as defined below;
$R_6$ is a hydrogen atom, an alkyl radical having from 1 to 12 carbon atoms;
s and t have the values 0, 1 or 2;
Z is an oxygen, nitrogen or sulfur atom;

$R_7$ is a hydrogen atom, an alkyl radical having from 1 to 12 carbon atoms, an aryl radical, an aralkyl radical, a heteroaryl radical or a heterocyclic radical;

$R_9$ is a radical O—$(CH_2)_v$—$R_{10}$, a hydroxyl radical, an alkoxy radical having from 1 to 7 carbon atoms, an aryl radical, an aralkyl radical, a heteroaryl radical, a heterocyclic radical, or the radical:

wherein $R_{10}$, R' and R" are as defined below;

R' is a hydrogen atom, an alkyl radical having from 1 to 12 carbon atoms, an aryl radical, an aralkyl radical, a heteroaryl radical or a heterocyclic radical or a hydroxyl radical;

R" is a hydrogen atom, an alkyl radical having from 1 to 12 carbon atoms, an aryl radical, an aralkyl radical, optionally substituted with one or more halogen atoms, a heteroaryl radical, a heterocyclic radical or a radical $(CH_2)_v$—$R_{10}$, wherein $R_{10}$ and v are as defined below;

$R_{10}$ is an aryl, aralkyl or heteroaryl radical, a heterocyclic radical, the radical NH—CO—$R_{11}$, the radical NH—CO—O—$R_{11}$, the radical N—$R_{11}R_{12}$ or the radical CH—$R_{11}R_{12}$; v has the value 1, 2 or 3;

$R_{11}$ is a hydrogen atom, an alkyl radical having from 1 to 12 carbon atoms, an aryl radical, an aralkyl radical, a heteroaryl radical or a heterocyclic radical;

$R_{12}$ is a hydrogen atom or an alkyl radical having from 1 to 3 carbon atoms;

A is a radical having the following structure:

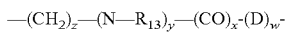

or

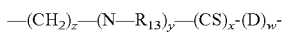

wherein D, w, x, y, z and $R_{13}$ are as defined below;

D is an oxygen or sulfur atom, a radical —$NR_{14}$ or a $CH_2$ radical;

$R_{14}$ is as defined below;

x and y each have the value of 1;

z has the value of 0 or 1;

w has a value from 0 to 6 with the proviso that w is equal to 0 or 1 when D is oxygen, and $R_{13}$ and $R_{14}$ are each a hydrogen atom or an alkyl radical having from 1 to 12 carbon atoms; and $R_{15}$ is a hydrogen atom or an alkyl radical having from 1 to 7 carbon atoms.

2. An alkali metal or alkaline-earth metal, zinc or organic amine salt of the biaromatic compound as defined by claim 1.

3. The biaromatic compound as defined by claim 1, bearing at least one substituent selected from the group consisting of methyl, ethyl and propyl radicals.

4. The biaromatic compound as defined by claim 1, bearing at least one substituent selected from the group consisting of isopropyl, butyl, tert-butyl, hexyl, heptyl, octyl, decyl and cyclohexyl radicals.

5. The biaromatic compound as defined by claim 1, bearing at least one substituent selected from the group consisting of methoxymethoxy, ethoxymethoxy and methoxyethoxymethoxy radicals.

6. The biaromatic compound as defined by claim 1, bearing at least one substituent selected from the group consisting of fluorine, chlorine and bromine atoms.

7. The biaromatic compound as defined by claim 1, bearing at least one substituent selected from the group consisting of methoxy, ethoxy, isopropyloxy, tert-butoxy, hexyloxy, benzyloxy and phenoxy radicals, which may optionally be substituted with an alkyl radical having from 1 to 12 carbon atoms.

8. The biaromatic compound as defined by claim 1, bearing at least one substituent selected from the group consisting of phenyl, biphenyl, cinnamyl and naphthyl radicals, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

9. The biaromatic compound as defined by claim 1, bearing at least one substituent selected from the group consisting of benzyl, phenethyl and 2-naphthylmethyl radicals, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

10. The biaromatic compound as defined by claim 1, bearing at least one substituent selected from the group consisting of pyridyl, furyl, thienyl, isoxazolyl, oxadiazolyl, oxazolyl, benzimidazolyl, indolyl and benzofuran radicals, optionally substituted with at least one halogen, an alkyl radical having from 1 to 12 carbon atoms, an alkoxy radical having from 1 to 7 carbon atoms, an aralkoxy radical or an aryloxy radical, an aryl radical, a nitro function, a polyether radical, an aryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

11. The biaromatic compound as defined by claim 1, bearing at least one substituent selected from the group consisting of morpholino, piperidino, piperazino, 2-oxo-1-piperidyl and 2-oxo-1-pyrrolidinyl radicals, optionally substituted with at least one alkyl radical having from 1 to 12 carbon atoms, an alkoxy radical having from 1 to 7 carbon atoms, an aralkoxy radical or an aryloxy radical, an aryl radical, a nitro function, a polyether radical, an aryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

12. The biaromatic compound as defined by claim 1, having at least one of the following definitions:

R and $R_3$, which may be identical or different, are each a hydrogen atom or a fluorine atom;

$R_{15}$ is an hydrogen atom or a methyl radical;

$R_9$ is a hydroxyl radical or a radical NR'R";

A is a linking radical of structure —$CH_2$—$N(R_{13})$—CO— or $N(R_{13})$—$(CO)_x(D)_w$, wherein w=0 or 1 and x=1;

$R_4$ is an alkyl or aryl radical.

13. The biaromatic compound as defined by claim 1, having at least one of the following characteristics:

R and $R_3$, which may be identical or different, are each a hydrogen atom or a fluorine atom;

$R_{15}$ is a hydrogen atom or a methyl radical;

$R_9$ is a hydroxyl radical;

A is a linking radical of structure —$CH_2$—$N(R_{13})$—CO— or $N(R_{13})_y$—$(CO)_x(D)_w$, wherein y=1, w=1 and x=1, D is a radical —$NR_{14}$ and $R_{14}$ is a hydrogen atom;

$R_4$ is a naphthyl radical.

14. The biaromatic compound as defined by claim 1, selected from the group consisting of:

(i). (S)-3-{3'-[(benzoylmethylamino)methyl]biphenyl-4-yl}-2-(1-methyl-3-oxo-3-phenylpropenylamino)propionic acid; and (p). 3-{3'-[(benzoylmethylamino)methyl]biphenyl-4-yl}-2-(1-methyl-3-oxo-3-phenylpropenylamino)propionic acid;

or mixtures thereof.

15. A pharmaceutical composition comprising a biaromatic compound as defined by claim 1 and a physiologically acceptable support therefor.

16. A cosmetic composition comprising a biaromatic compound as defined by claim 1 and cosmetically acceptable support therefor.

* * * * *